(12) United States Patent
Wagner

(10) Patent No.: US 10,201,374 B2
(45) Date of Patent: Feb. 12, 2019

(54) ASSEMBLY TOOL FOR A PROSTHESIS

(71) Applicant: Zimmer, Inc., Warsaw, IN (US)

(72) Inventor: Terry W. Wagner, Mishawaka, IN (US)

(73) Assignee: Zimmer, Inc., Warsaw, IN (US)

( * ) Notice: Subject to any disclaimer, the term of this patent is extended or adjusted under 35 U.S.C. 154(b) by 1370 days.

(21) Appl. No.: 13/800,650

(22) Filed: Mar. 13, 2013

(65) Prior Publication Data

US 2013/0340236 A1   Dec. 26, 2013

Related U.S. Application Data

(60) Provisional application No. 61/663,452, filed on Jun. 22, 2012.

(51) Int. Cl.
  *B25B 27/14* (2006.01)
  *A61B 17/56* (2006.01)
  (Continued)

(52) U.S. Cl.
  CPC .............. *A61B 17/56* (2013.01); *A61F 2/384* (2013.01); *A61F 2/3804* (2013.01);
  (Continued)

(58) Field of Classification Search
  USPC ....... 269/270, 278; 606/90, 99, 105; 29/270, 29/278
  See application file for complete search history.

(56) References Cited

U.S. PATENT DOCUMENTS 750,678 A     1/1904   Morton
1,110,528 A   9/1914   Borresen
(Continued)

FOREIGN PATENT DOCUMENTS

CN   104602648 A   5/2015
DE     7144144 U   3/1972
(Continued)

OTHER PUBLICATIONS

"U.S. Appl. No. 12/856,112, Non Final Office Action dated Mar. 14, 2014", 10 pgs.
(Continued)

*Primary Examiner* — Joseph J Hail
*Assistant Examiner* — Shantese McDonald
(74) *Attorney, Agent, or Firm* — Schwegman Lundberg & Woessner, P.A.

(57) ABSTRACT

An assembly tool for assembling components of an implant can include a finger assembly, a handle assembly, and a crossbar assembly. The finger assembly can include first and second fingers oriented parallel to each other, and sized and shaped to releasably engage first and second components of the implant during assembly. The handle assembly can include first and second handles pivotally connected to each other and configured to control movement of the first and second fingers. The crossbar assembly can be configured to maintain the first and second fingers substantially parallel to each other during movement of the first and second fingers. The assembly tool can be used for assembling a bearing assembly to an ulnar component of an elbow prosthesis.

17 Claims, 17 Drawing Sheets

(51) Int. Cl.
*A61F 2/46* (2006.01)
*A61F 2/38* (2006.01)
*A61F 2/30* (2006.01)

(52) U.S. Cl.
CPC .. *A61F 2/4637* (2013.01); *A61F 2002/30507* (2013.01); *A61F 2002/30624* (2013.01); *A61F 2002/3813* (2013.01); *Y10T 29/49876* (2015.01); *Y10T 29/539* (2015.01)

(56) References Cited

U.S. PATENT DOCUMENTS

| | | | |
|---|---|---|---|
| 1,517,162 A | 11/1924 | King | |
| 1,677,365 A | 7/1928 | Peck | |
| 2,462,536 A | 2/1949 | Muter | |
| 2,737,917 A | 3/1956 | Steele | |
| 2,837,951 A | 6/1958 | Phelps | |
| 3,157,075 A | 11/1964 | Filia | |
| 3,187,751 A | 6/1965 | Coren | |
| 3,563,124 A | 2/1971 | Gargrave | |
| 3,641,652 A | 2/1972 | Arnold et al. | |
| 3,708,805 A | 1/1973 | Scales et al. | |
| 3,816,854 A | 6/1974 | Schlein | |
| 3,826,160 A | 7/1974 | Allen et al. | |
| 4,038,704 A | 8/1977 | Ring | |
| 4,227,299 A | 10/1980 | Kuehling | |
| 4,280,231 A | 7/1981 | Swanson | |
| 4,306,550 A | 12/1981 | Forte | |
| 4,365,411 A | 12/1982 | Muldoon | |
| 4,383,337 A | 5/1983 | Volz et al. | |
| 4,420,879 A | 12/1983 | Harringer | |
| 4,587,964 A | 5/1986 | Walker et al. | |
| 4,765,328 A | 8/1988 | Keller et al. | |
| 4,822,364 A | 4/1989 | Inglis et al. | |
| 4,982,631 A | 1/1991 | Lowther | |
| 5,020,399 A | 6/1991 | Annis et al. | |
| RE33,714 E * | 10/1991 | Anderson | B25B 7/12 30/363 |
| 5,061,271 A | 10/1991 | Van Zile | |
| 5,197,368 A | 3/1993 | Meyer et al. | |
| 5,314,479 A | 5/1994 | Rockwood, Jr. et al. | |
| 5,376,121 A | 12/1994 | Huene et al. | |
| 5,702,457 A | 12/1997 | Walch et al. | |
| 5,702,486 A | 12/1997 | Craig et al. | |
| 5,723,015 A | 3/1998 | Risung et al. | |
| 5,961,555 A | 10/1999 | Hubner | |
| 6,027,534 A | 2/2000 | Wack et al. | |
| 6,102,953 A | 5/2000 | Huebner | |
| 6,129,764 A | 10/2000 | Servidio | |
| 6,168,630 B1 | 1/2001 | Keller et al. | |
| 6,197,063 B1 | 3/2001 | Dews | |
| 6,290,725 B1 | 9/2001 | Weiss et al. | |
| 6,314,843 B1 | 11/2001 | Wiebe et al. | |
| 6,379,387 B1 | 4/2002 | Tornier | |
| 6,673,114 B2 | 1/2004 | Hartdegen et al. | |
| 6,699,290 B1 | 3/2004 | Wack et al. | |
| 6,716,218 B2 * | 4/2004 | Holmes | A61B 17/8866 606/105 |
| 6,716,248 B2 | 4/2004 | Huene | |
| 6,739,068 B1 | 5/2004 | Rinner | |
| 6,767,368 B2 | 7/2004 | Tornier | |
| 6,890,357 B2 | 5/2005 | Tornier | |
| 6,923,832 B1 | 8/2005 | Sharkey et al. | |
| 6,964,088 B2 | 11/2005 | Crevoisier | |
| 6,969,407 B2 | 11/2005 | Klotz et al. | |
| 7,097,663 B1 | 8/2006 | Nicol et al. | |
| 7,247,170 B2 | 7/2007 | Graham et al. | |
| 7,338,528 B2 | 3/2008 | Stone et al. | |
| 7,604,666 B2 | 10/2009 | Berelsman et al. | |
| 7,625,406 B2 | 12/2009 | Berelsman et al. | |
| 7,722,625 B2 | 5/2010 | Sanders et al. | |
| 7,846,376 B2 | 12/2010 | Abt et al. | |
| 7,850,737 B2 | 12/2010 | Morrey | |
| 8,328,873 B2 | 12/2012 | Metzger et al. | |
| 8,753,348 B2 * | 6/2014 | DiDomenico | A61B 17/8019 606/105 |
| 8,936,647 B2 | 1/2015 | Wagner et al. | |
| 8,968,411 B2 | 3/2015 | Wagner et al. | |
| 2001/0021876 A1 | 9/2001 | Terril-Grisoni et al. | |
| 2002/0156534 A1 | 10/2002 | Grusin et al. | |
| 2002/0165614 A1 | 11/2002 | Tornier | |
| 2003/0144739 A1 | 7/2003 | Huene | |
| 2003/0208276 A1 | 11/2003 | Berelsman et al. | |
| 2003/0208277 A1 | 11/2003 | Weiss et al. | |
| 2004/0186581 A1 | 9/2004 | Huene | |
| 2004/0193268 A1 | 9/2004 | Hazebrouck | |
| 2004/0193276 A1 | 9/2004 | Maroney et al. | |
| 2004/0243243 A1 | 12/2004 | Tornier | |
| 2005/0043806 A1 | 2/2005 | Cook et al. | |
| 2005/0075735 A1 | 4/2005 | Berelsman et al. | |
| 2006/0100712 A1 | 5/2006 | Ball | |
| 2006/0100713 A1 | 5/2006 | Ball | |
| 2006/0111788 A1 | 5/2006 | Ball | |
| 2006/0111789 A1 | 5/2006 | Ball | |
| 2006/0173546 A1 | 8/2006 | Berelsman et al. | |
| 2006/0224243 A1 | 10/2006 | Pare et al. | |
| 2006/0247786 A1 | 11/2006 | Ball | |
| 2007/0129808 A1 | 6/2007 | Justin et al. | |
| 2007/0282450 A1 | 12/2007 | Habermeyer et al. | |
| 2007/0299527 A1 | 12/2007 | Mccleary et al. | |
| 2008/0015706 A1 | 1/2008 | Berelsman et al. | |
| 2008/0033566 A1 | 2/2008 | Berelsman et al. | |
| 2008/0114461 A1 | 5/2008 | Collazo | |
| 2008/0306601 A1 | 12/2008 | Dreyfuss | |
| 2009/0024221 A1 | 1/2009 | Ball | |
| 2009/0105839 A1 | 4/2009 | Ikegami et al. | |
| 2009/0312840 A1 | 12/2009 | Morrey | |
| 2010/0051141 A1 | 3/2010 | Bhambri | |
| 2010/0087928 A1 | 4/2010 | Graham et al. | |
| 2010/0160985 A1 * | 6/2010 | Pannu | A61B 17/025 606/86 A |
| 2010/0179661 A1 | 7/2010 | Berelsman et al. | |
| 2010/0222887 A1 | 9/2010 | Katrana et al. | |
| 2011/0125274 A1 | 5/2011 | Bartel et al. | |
| 2011/0153024 A1 | 6/2011 | Wagner et al. | |
| 2011/0172781 A1 | 7/2011 | Katrana et al. | |
| 2012/0000326 A1 | 1/2012 | Sheriff | |
| 2012/0095473 A1 * | 4/2012 | Soliman | A61B 17/158 606/88 |
| 2013/0345818 A1 | 12/2013 | Wagner et al. | |
| 2014/0012338 A1 * | 1/2014 | Kirschman | A61B 17/808 606/86 A |
| 2014/0165793 A1 * | 6/2014 | Legg | B21F 15/04 81/319 |
| 2015/0088263 A1 | 3/2015 | Wagner et al. | |

FOREIGN PATENT DOCUMENTS

| | | |
|---|---|---|
| EP | 2863845 A1 | 4/2015 |
| FR | 2575384 A1 | 7/1986 |
| FR | 2579454 A1 | 10/1986 |
| FR | 2660857 B1 | 12/1997 |
| WO | WO-8904238 A1 | 5/1989 |
| WO | WO-9725943 A1 | 7/1997 |
| WO | WO-2006129495 A1 | 12/2006 |
| WO | WO-2008002545 A2 | 1/2008 |
| WO | WO-2010098791 A2 | 9/2010 |
| WO | WO-2011060430 A2 | 5/2011 |
| WO | WO-2013192408 A1 | 12/2013 |

OTHER PUBLICATIONS

"U.S. Appl. No. 12/856,112, Notice of Allowance dated Oct. 24, 2014", 8 pgs.

"U.S. Appl. No. 12/856,112, Response filed Jun. 16, 2014 to Non-Final Office Action dated Mar. 14, 2014", 11 pgs.

"U.S. Appl. No. 13/800,567, Non Final Office Action dated Jan. 29, 2014", 14 pgs.

"U.S. Appl. No. 13/800,567, Notice of Allowance dated Sep. 3, 2014", 10 pgs.

(56) References Cited

OTHER PUBLICATIONS

"U.S. Appl. No. 13/800,567, Response filed May 29, 2014 to Non Final Office Action dated Jan. 29, 2014", 19 pgs.
"U.S. Appl. No. 14/559,121, Prleliminary Amendment filed Dec. 4, 2014", 7 pgs.
"International Application Serial No. PCT/US2013/046792, International Preliminary Report on Patentability dated Dec. 31, 2014", 9 pgs.
"U.S. Appl. No. 14/559,121, Non Final Office Action dated Feb. 11, 2016", 7 pgs.
"U.S. Appl. No. 14/559,121, Notice of Allowance dated Jun. 28, 2016", 5 pgs.
"U.S. Appl. No. 14/559,121, Response filed May 11, 2016 to Non Final Office Action dated Feb. 11, 2016", 8 pgs.
"U.S. Appl. No. 14/559,121, Response filed Nov. 2, 2015 to Restriction Requirement dated Sep. 2, 2015", 11 pgs.
"U.S. Appl. No. 14/559,121, Restriction Requirement dated Sep. 2, 2015", 7 pgs.
"Chinese Application Serial No. 201380042656.3, Office Action dated Oct. 8, 2015", (W/ English Translation), 16 pgs.
"Chinese Application Serial No. 201380042656.3, Response filed Mar. 23, 2016 to Office Action dated Oct. 8, 2015", (W English Translation), 16 pgs.
"U.S. Appl. No. 15/278,982, Final Office Action dated Jan. 26, 2018", 16 pgs.
"U.S. Appl. No. 15/278,982, Response filed Dec. 5, 2017 to Non Final Office Action dated Sep. 5, 2017", 13 pgs.
"U.S. Appl. No. 12/856,112, Advisory Action dated Aug. 15, 2013", 3 pgs.
"U.S. Appl. No. 12/856,112, Response filed Aug. 23, 2013 to Final Office Action dated Apr. 26, 2013 and Advisory Action dated Aug. 15, 2013", 12 pgs.
"U.S. Appl. No. 13/800,567, Response filed Oct. 9, 2013 to Restriction Requirement dated Sep. 10, 2013", 10 pgs.
"U.S. Appl. No. 13/800,567, Restriction Requirement dated Sep. 10, 2013", 7 pgs.
"International Application Serial No. PCT/US2013/046792, International Search Report dated Aug. 23, 2013", 6 pgs.
"International Application Serial No. PCT/US2013/046792, Written Opinion dated Aug. 23, 2013", 7 pgs.
"U.S. Appl. No. 12/856,112, Examiner Interview Summary dated Jul. 11, 2013", 3 pgs.
"U.S. Appl. No. 12/856,112, Examiner Interview Summary dated Dec. 17, 2012", 5 pgs.
"U.S. Appl. No. 12/856,112, Final Office Action dated Apr. 26, 2013", 9 pgs.
"U.S. Appl. No. 12/856,112, Non Final Office Action dated May 30, 2012", 11 pgs.
"U.S. Appl. No. 12/856,112, Response filed May 14, 2012 to Restriction Requirement dated Apr. 13, 2012", 9 pgs.
"U.S. Appl. No. 12/856,112, Response filed Jul. 1, 2013 to Final Office Action dated Apr. 26, 2013", 12 pgs.
"U.S. Appl. No. 12/856,112, Response filed Nov. 30, 2012 to Non Final Office Action dated May 30, 2012", 18 pgs.
"U.S. Appl. No. 12/856,112, Restriction Requirement dated Apr. 13, 2012", 7 pgs.
"The Ball Lock System—Dayton True Position Retainers", Brochure; Dayton Progress Corporation, (2002), 6 pgs.
"Zimmer Coonrad/Morrey Total Elbow Arthroplastly—Impaction Grafting Procedure", Surgical Technique for Revision; Zimmer, Inc., (2002), 2 pgs.
"Zimmer Coonrad/Morrey Total Elbow, Interchangeability, Anterior Flange, Clinical History", Surgical Technique; 97-8106-102-00 Rev. 2, Zimmer, Inc., (2002, 2005, 2009), 11 pgs.
"Zimmer Coonrad/Morrey Total Elbow, Interchangeability, Anterior Flange, Clinical Success", Brochure; 97-8106-301-00 Zimmer, Inc., (2000, 2006, 2007), 4 pgs.

* cited by examiner

ASSEMBLY TOOL FOR A PROSTHESIS

CROSS-REFERENCE TO RELATED APPLICATION(S)

This application claims the benefit of priority under 35 U.S.C. § 119(e) of Wagner et al., U.S. Provisional Patent Application Ser. No. 61/663,452, entitled "MODULAR ELBOW PROSTHESIS," filed on Jun. 22, 2012, which is herein incorporated by reference in its entirety.

This application is related to U.S. Ser. No. 13/800,567, filed on the same day as this application, entitled "ELBOW PROSTHESIS."

TECHNICAL FIELD

The present patent application relates to orthopedic prostheses, and more particularly, to a tool and methods for assembling a modular prosthesis.

BACKGROUND

A joint arthroplasty procedure may be performed to repair or replace damaged bone of a patient's joint, such as bone that is damaged due to a traumatic injury or a degenerative illness. For example, during a total elbow arthroplasty procedure, the surgeon implants a prosthetic humeral component into the distal end of a patient's humerus and a prosthetic ulnar component into the proximal end of the patient's ulna. The prosthetic humeral component and the prosthetic ulnar component are generally joined by a hinge that enables pivoting movement between the prosthetic humeral component and the prosthetic ulnar component, to recreate the natural, anatomical articulation of the elbow joint.

Orthopedic prostheses, such as the above-mentioned elbow prosthesis having a humeral component and an ulnar component, can be modular and one or both of the components can have a plurality of individual pieces. In some cases, assembling the components and the prosthesis can be difficult given, for example, the complexity of the design and/or a small size of the components and pieces.

OVERVIEW

The present inventors recognize, among other things, an opportunity for an assembly tool that aids in assembling a modular prosthesis and/or a component of the prosthesis. The assembly tool described herein can be used, for example, in a joint arthroplasty procedure or in a revision procedure.

To better illustrate the assembly tool and methods disclosed herein, the following non-limiting examples are provided:

In an example, an assembly tool for assembling components of an implant comprises a finger assembly, a handle assembly, and a crossbar assembly connected to the finger assembly and the handle assembly. The finger assembly can comprise a first finger sized and shaped to releasably engage a first component of the implant and a second finger sized and shaped to releasably engage a second component of the implant, the first and second fingers oriented substantially parallel to each other. The handle assembly can comprise a first handle pivotally connected to a second handle, the handle assembly configured to control movement of the first and second fingers when the first and second handles are actuated. The crossbar assembly can be configured to maintain the first and second fingers substantially parallel to each other during movement of the first and second fingers by actuation of the first and second handles.

In an example, an assembly tool for assembling a multi-component implant comprises a first finger including a first attachment feature configured to releasably secure a first component of the implant to the first finger and a second finger including a second attachment feature configured to releasably secure a second component of the implant to the second finger, wherein the first and second fingers are oriented substantially parallel to each other. The assembly tool further comprises a handle assembly comprising a first handle pivotally connected to a second handle, the handle assembly configured to control movement of the first and second fingers when the first and second handles are actuated. The assembly tool further comprises a first finger extension extending from the first finger and connected to the second handle, a second finger extension extending from the second finger and connected to the first handle, and a crossbar assembly comprising a first crossbar pivotally connected to a second crossbar. The crossbar assembly can be configured to maintain the first and second fingers substantially parallel to each other throughout movement of the first and second fingers by actuation of the first and second handles.

In an example, a method of assembling a multi-component implant using an assembly tool comprises mounting a first component of the implant onto a first finger of the assembly tool such that the first finger releasably engages the first component to the assembly tool and mounting a second component of the implant onto a second finger of the assembly tool such that the second finger releasably engages the second component to the assembly tool. The method further comprises moving the first and second fingers towards each other and into a compressed position to attach the first component to the second component, maintaining a substantially parallel relationship between the first and second fingers throughout movement of the first and second fingers, and releasing the first and second fingers from the compressed position back to a relaxed position.

This overview is intended to provide a summary of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The present application relates to devices and methods for an assembly tool that can be used before or during an orthopedic procedure involving a prosthesis. The assembly tool can be used to aid in assembling all or a portion of the prosthesis.

For illustrative purposes, FIGS. 1-6 illustrate an example of an elbow prosthesis 100 that can be used in an elbow arthroplasty procedure and can include a humeral component 102 and an ulnar component 104. The elbow prosthesis 100 is an example of an implant or prosthesis that can be assembled using an assembly tool as described herein and shown in FIGS. 7-15. Reference is made to a co-pending application filed the same day as this application, U.S. application Ser. No. 13/800,567, entitled "ELBOW PROSTHESIS."

Figure 1:
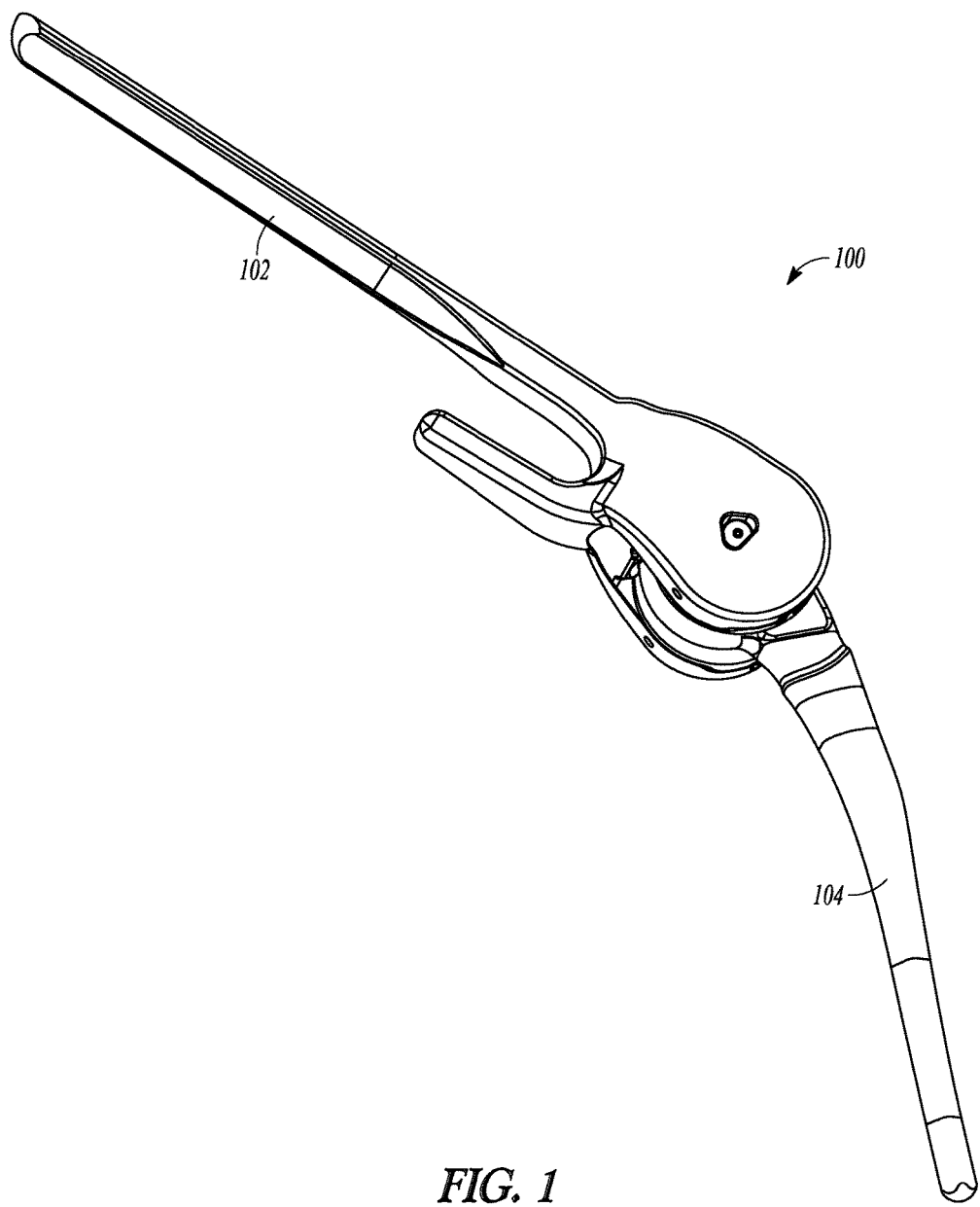
FIG. 1 is a perspective view of an example of an elbow prosthesis.

The elbow prosthesis 100, as shown in FIG. 1, is oriented anatomically (i.e. how the elbow prosthesis 10 would be oriented if implanted in a body of a patient) and the ulnar component 104 is at an angle of approximately forty-five (45) degrees, relative to the humeral component 102. The humeral component 102 can be partially received within a humeral medullary canal, and the ulnar component 104 can be partially received within an ulnar medullary canal. The elbow prosthesis 100 can include a suitable connection means that can allow for pivoting movement of the ulnar component 104 relative to the humeral component 102.

Figure 2:
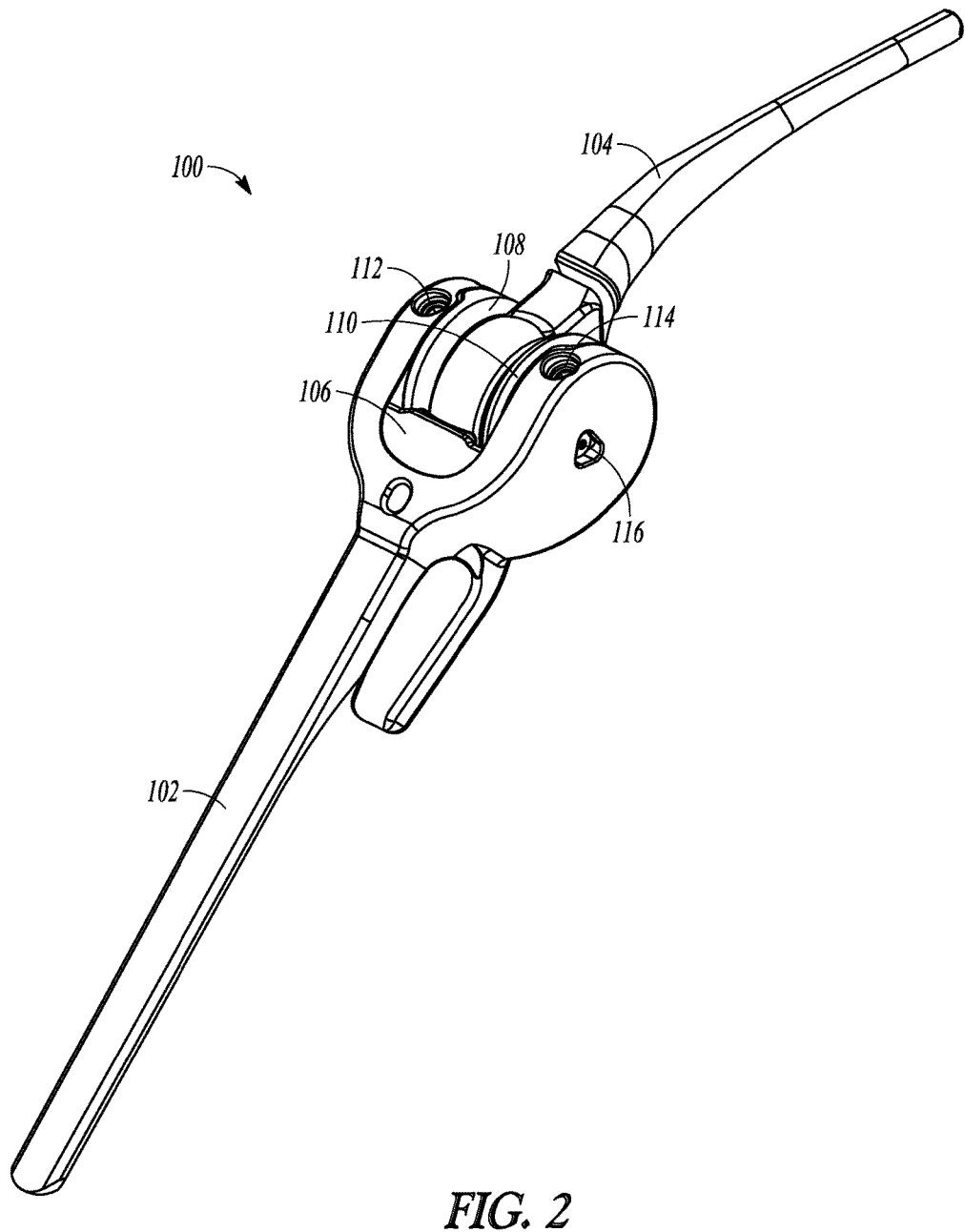
FIG. 2 is a perspective view of the elbow prosthesis of FIG. 1, rotated approximately 180 degrees.

FIG. 2 shows the elbow prosthesis 100 rotated approximately 180 degrees relative to what is shown in FIG. 1. The elbow prosthesis 100 can include the humeral component 102, the ulnar component 104, a humeral bearing 106, a first ulnar bearing 108, a second ulnar bearing 110, a first fastener 112, a second fastener 114, and a pin 116. Each of these components is also shown in FIG. 3, which is an exploded view of the elbow prosthesis 100 shown in FIG. 2.

Figure 3:
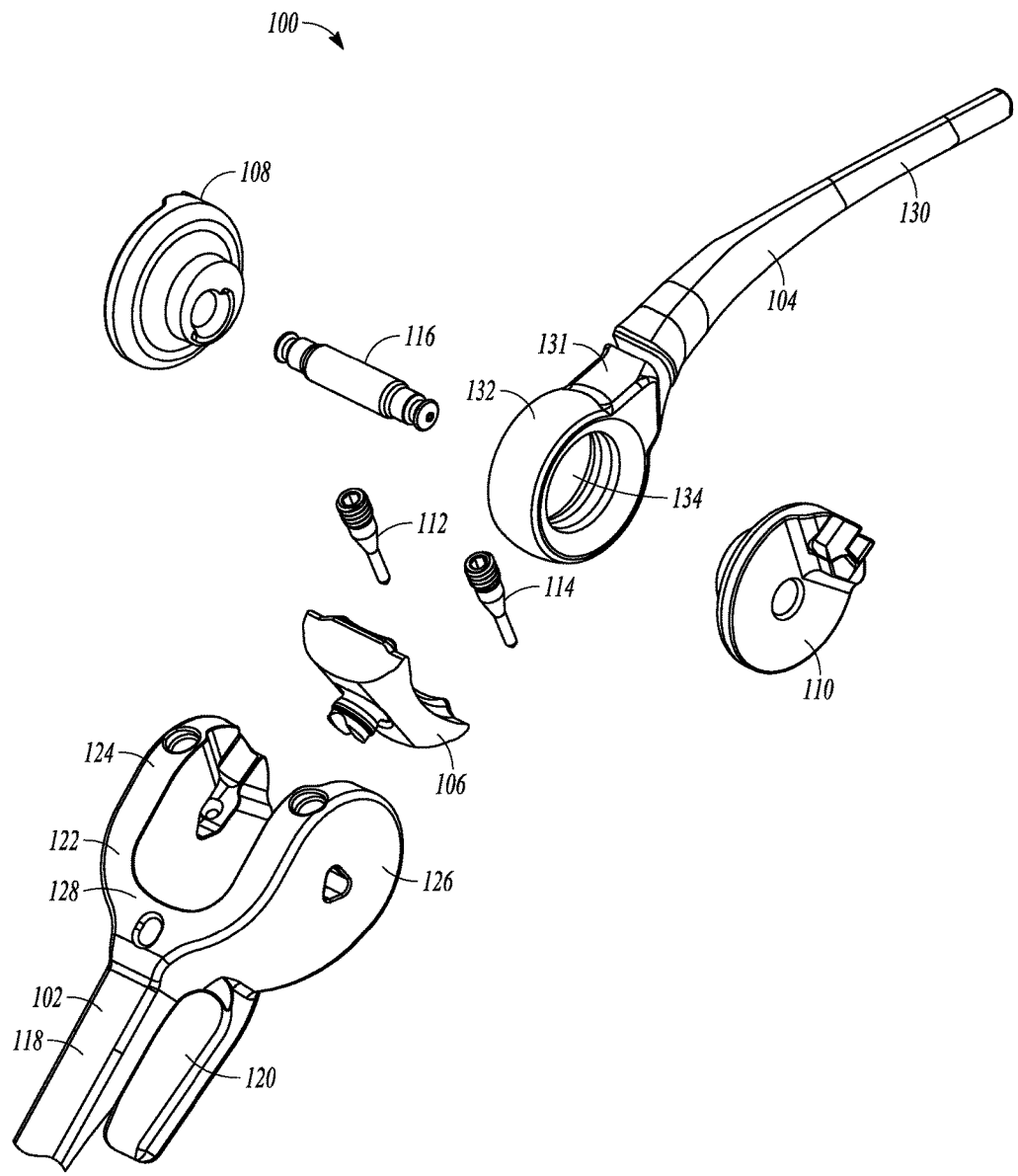
FIG. 3 is an exploded perspective view of the elbow prosthesis of FIG. 2.

With reference to FIG. 3, the humeral component 102 can include a humeral stem 118, a flange 120, and a yoke 122 extending from the humeral stem 118. The yoke 122 can include a first ear 124 and a second ear 126. The humeral bearing 106 can be positioned in or coupled to a base 128 of the yoke 122.

The ulnar component 104 can include an ulnar stem 130, an ulnar head 132 having an aperture or opening 134 extending through the ulnar head 132, and an ulnar neck 131 between the head 132 and the stem 130. The ulnar head 132 can also be referred to as an ulnar eye.

Each of the first 108 and second 110 ulnar bearings can extend into the aperture 134 of the ulnar head 132. The pin 116 can extend through the first ulnar bearing 108, the ulnar head 132, and the second ulnar bearing 110. Opposing end portions of the pin 116 can extend into the first 124 and second 126 ears of the yoke 122 of the humeral component 102. When assembled to the humeral component 102, the pin 116 can define an axis upon which the ulnar component 104 can pivot relative to the humeral component 102.

The first fastener 112 can extend into the first ear 124 of the yoke 122 and the second fastener 114 can extend into the second ear 126 of the yoke 122 to secure the humeral 102 and ulnar 104 components to each other. In an example, the first 112 and second 114 fasteners can be a first screw and a second screw, respectively. The engagement between the first fastener 112, the first ear 124, and the pin 116, as well as a similar engagement between the second fastener 114, the second ear 126, and the pin 116, is described in further detail below.

When the humeral component 102 and the ulnar component 104 are implanted into a humerus and an ulna, respectively, of a patient, the yoke 122 of the humeral component 102 and the ulnar head 132 of the ulnar component 104 can remain exposed. The ulnar head 132 can be configured to pivot about the pin 116 to enable movement of the ulnar component 104 relative to the humeral component 102, as described above.

Figure 4:
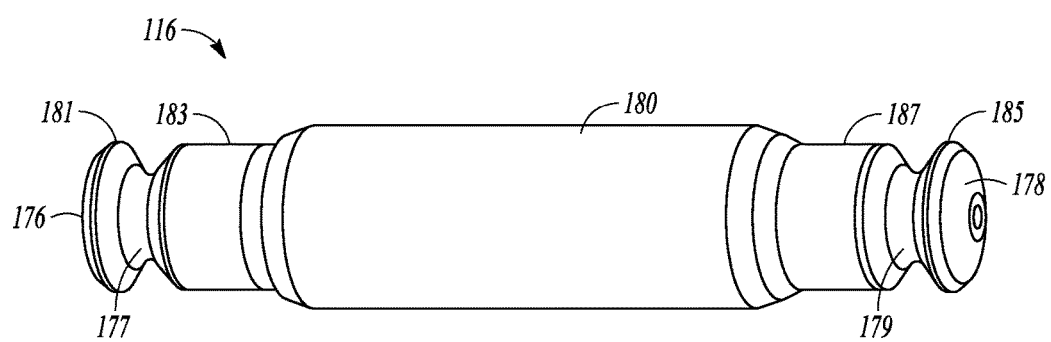
FIG. 4 is a perspective view of a pin of the elbow prosthesis of FIGS. 1-3.
Figure 6:
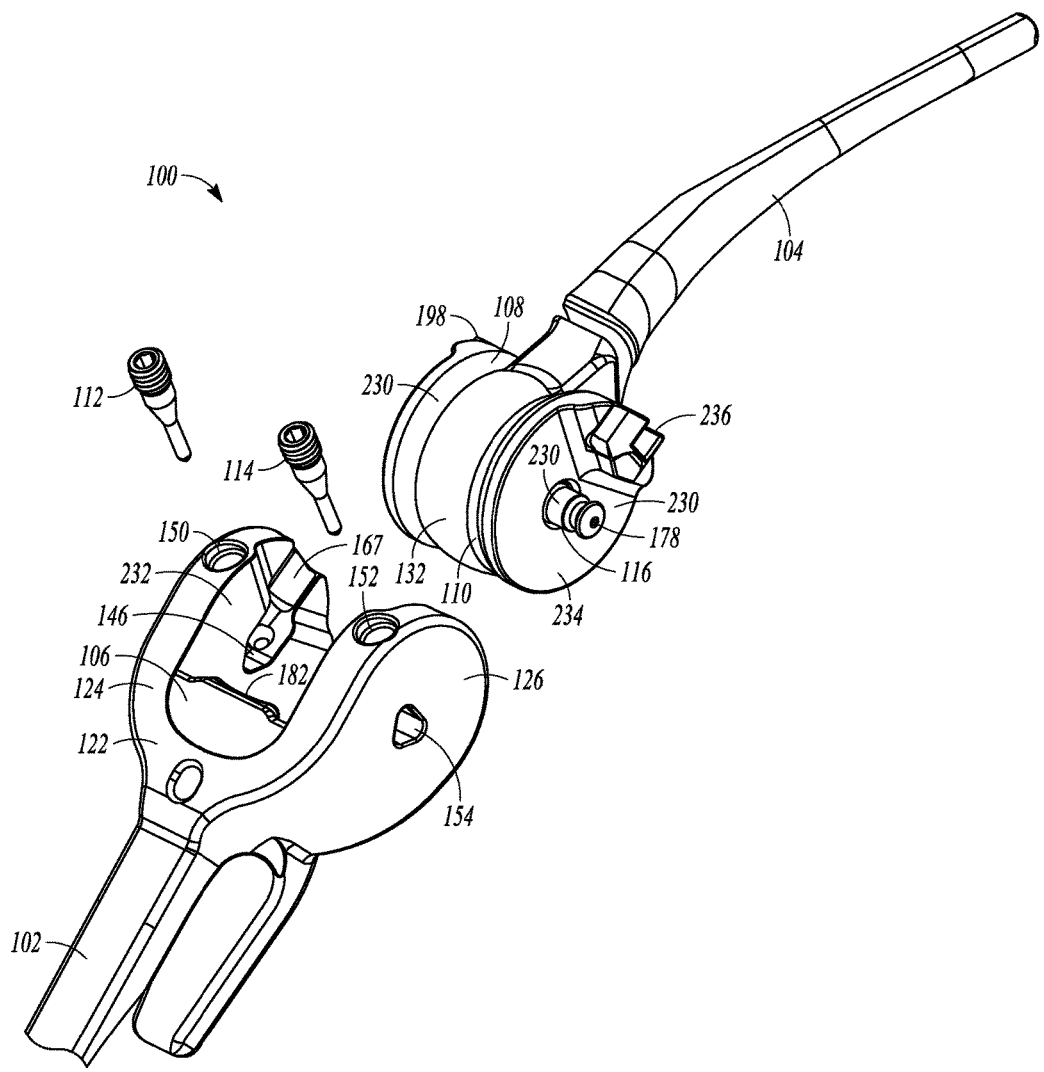
FIG. 6 is a perspective view of the elbow prosthesis of FIGS. 1-3 in a partially assembled state.

FIG. 4 is a perspective view of the pin 116, which can include a first end portion 176, a second end portion 178, and a main body portion 180. The first end portion 176 can include a first groove 177, a first outer diameter 181, and a first inner diameter 183. The second end portion 178 can include a second groove 179, a second outer diameter 185, and a second inner diameter 187. As shown in FIG. 6, the main body portion 180 can have a larger diameter than the inner diameters 183 and 187 and the outer diameters 181 and 185 of the first 176 and second 178 end portions.

The pin 116 can be made of one or more materials suitable for implantation within a human or animal body and for enabling pivoting movement of one component relative to another component. These materials can include, but are not limited to, stainless steel, titanium, cobalt, or one or more alloys thereof. In an example, the pin 116 can be cobalt chrome.

Figure 5A:
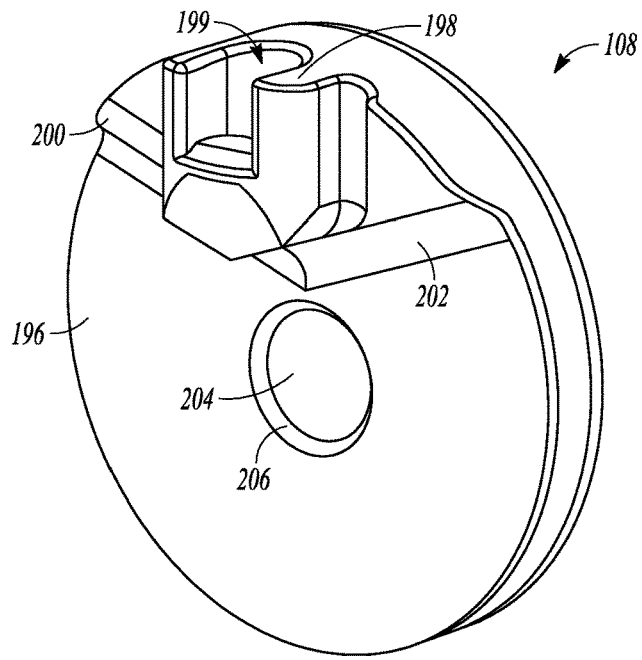
FIGS. 5A and 5B are perspective views of an ulnar bearing of the elbow prosthesis of FIGS. 1-3.
Figure 5B:
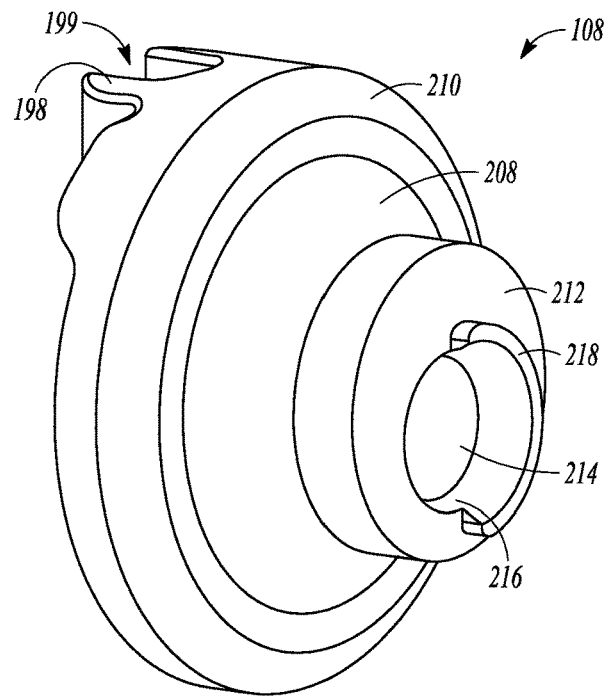

FIGS. 5A and 5B show two perspective views of the first ulnar bearing 108. FIG. 5B shows the first ulnar bearing 108 rotated approximately 90 degrees relative to the view shown in FIG. 5A. The first ulnar bearing 108 can include an external face 196, a tab 198, a slot 199, and shoulders 200 and 202 on each side of the tab 198. The external face 196 can be a seating surface between the first ulnar bearing 108 and the first ear 124 of the yoke 122.

The first ulnar bearing 108 can include a first opening or hole 204 for receiving the pin 116. In an example, the first hole 204 can include a chamfer 206 to help lead the pin 116 through the first hole 204. The pin 116 can have a press fit with the first and second ulnar bearings 108 and 110.

The first ulnar bearing 108 can include a first bearing extension 208 having an articulation surface 210 and an end face 212. A second opening or hole 214 can extend through the end face 212 for receiving the pin 116. In an example, the second hole 214 can include a chamfer 216 to help lead the pin 116 through the second hole 216. A compression rib 218 can extend from the end face 212 on at least a portion of the end face 212. The first 204 and second 214 holes can converge within the first ulnar bearing 108 so as to form a single continuous channel that is structured to allow passage of the pin 116.

In an example, the second ulnar bearing 110 can be substantially similar to the first ulnar bearing 108. When rotated by approximately 180 degrees relative to the position in FIG. 5A, the second ulnar bearing 110 can mate with the first ulnar bearing 108.

The humeral bearing 106 and/or the first 108 and second 110 ulnar bearings can be made of one or more materials suitable for implantation within a human or animal body. In an example, the humeral bearing 106 and/or the first 108 and second ulnar bearings 110 can be made of an elastomeric material, such as, for example, a ultrahigh molecular weight polyethylene (UHMWPE). In an example, the humeral bearing 106 can be formed from a crosslinked ultrahigh molecular weight polyethylene blend stabilized with Vitamin E, such as disclosed in U.S. Pat. No. 7,846,376. In an example, the first 108 and second 110 ulnar bearings can be formed from a crosslinked ultrahigh molecular weight polyethylene blend stabilized with Vitamin E, such as disclosed in U.S. Pat. No. 7,846,376. When formed from an elastomeric material, the bearings 106, 108 and 110 can be squeezed or compressed, for example to overcome an interference fit or press fit, and/or conform to a surrounding metal component.

FIG. 6 is a view of the elbow prosthesis 100 partially assembled. As shown in FIG. 6, a bearing assembly 230 can be assembled onto the ulnar head 132 of the ulnar component 104. The bearing assembly 230 can include the first ulnar bearing 108, the second ulnar bearing 110, and the pin 116. The first bearing extension 208 of the first ulnar bearing 108 (see FIG. 5B) can extend into the aperture 134 of the ulnar head 132. A second bearing extension on the second ulnar bearing 110 can extend into the aperture 134 such that when the bearing assembly 230 is assembled onto the ulnar head 132, the end face 212 of the first ulnar bearing 108 (see FIG. 5B) can contact an end face on the second ulnar bearing 110. The main body portion 180 of the pin 116 (see FIG. 4) can extend through the first ulnar bearing 108, the ulnar head 132, and the second ulnar bearing 110; the first end portion 176 (see FIG. 4) and the second end portion 178 of the pin 116 can remain exposed at this point in the assembly of the elbow prosthesis 100. When the first 108 and second 110 ulnar bearings are assembled onto the pin 116, the end faces can contact one another; in an example, a compression of the first 108 and second 110 ulnar bearings with one another can occur at a later step when the bearings 108 and 110 and the ulnar component 104 can be attached to the humeral component 102.

A next step in the assembly of the elbow prosthesis 100 can include connecting the ulnar component 104 to the humeral component 102, which can include placing the first end portion 176 of the pin 116 into the first ear 124 of the yoke 122 and placing the second end portion 178 of the pin 116 into the second ear 126 of the yoke 122. The pin 116 and the first 124 and second 126 ears of the yoke 122 are each configured such that the first end portion 176 of the pin 116 can be secured inside the opening 146 formed in the first ear 124 and the second end portion 178 of the pin 116 can be secured inside the opening 154 formed in the second ear 126.

As described above, the first 108 and second 110 ulnar bearings can be formed of one or more elastomeric or compressible materials such the first 108 and second 110 ulnar bearings can be squeezed or compressed together as the bearing assembly 230 and the ulnar component 104 are assembled onto the humeral component 102. In an example, when the first 108 and second 110 ulnar bearings are squeezed together, the compression rib 218 on the first ulnar bearing 108 (see FIG. 5B) can compress against an end face on the second ulnar bearing 110, and a compression rib on the second ulnar bearing 110 can compress against the end face 212 on the first ulnar bearing 108 (see FIG. 5B). In an example, the compression ribs can each be generally semi-circular such that the when the end faces of the first 108 and second 110 ulnar bearings are in contact, the compression ribs together form a generally circular shape.

Once the ulnar bearing assembly 230 is attached to the humeral component 102, the first 108 and second 110 ulnar bearings can be secured within the yoke 122. In an example, the external face 196 of the first ulnar bearing 108 (see FIG. 5A) can contact an inner surface 232 of the first ear 124, and an external face 234 on the second ulnar bearing 110 can contact an inner surface of the second ear 126. The tab 198 on the first ulnar bearing (see FIG. 5A) can be press fit into the recess 167 formed in the upper portion of the first ear 124; a tab 236 on the second ulnar bearing 110 can be press fit into a similar recess formed in the upper portion of the second ear 126. In an example, the tab 198 on the first ulnar bearing 108 can be compressed during insertion of the tab 198 into the recess 167, until the tab 198 is through an opening of the recess 167, at which point the tab 198 can relax and conform to a space within the recess 167. Surface contour features formed on the inside walls of the recesses in the first 124 and second 126 ears can facilitate this press-fit.

A next step in the assembly of the elbow prosthesis 100 can include inserting the first fastener 112 through the bore 150 of the first ear 124 and inserting the second fastener 114 through the bore 152 of the second ear 126. Once the assembly is complete, the ulnar component 104 can pivot about the pin 116 such as to provide pivotal movement of the ulnar component 104 relative to the humeral component 102. As the ulnar component 104 moves, the ulnar head 132 can articulate against the articulation surface 182 of the humeral bearing 106.

The assembly of the elbow prosthesis 100 can be configured such that the bearings 106, 108 and 110, or at least one feature on the bearings 106, 108 and 110, can compress during an assembly of the elbow prosthesis 100 and then relax and conform to a surrounding area. Various features on the ulnar bearings 108 and 110, such as the tabs described above, or features on the humeral bearing 106 can allow an interference fit or press fit that can result in a stable placement of the bearings in the elbow prosthesis 100, such as to reduce or eliminate any movement of the bearings 106, 108, and 110 within the elbow prosthesis 100, particularly as various forces or loads are placed on the bearings 106, 108, and 110. In certain examples, alternative or additional features to those described herein can be used on the bearings 106, 108, 110 to provide a press fit.

The elbow prosthesis 100 is an example of a modular prosthesis having a plurality of components that can be assembled together. The assembly of the elbow prosthesis 100 can take place outside of the patient's body, or some or all of the assembly can take place after the ulnar 104 and/or humeral 102 components have been inserted into the ulnar and humeral medullary canals, respectively. The ulnar component 104, once assembled, can include the bearing assembly 230 and the pin 116. As described above, the first 108 and second 110 ulnar bearings of the bearing assembly 230 can include features to create an interference fit between the first 108 and second 110 bearings; moreover, the pin 116 and the first 108 and second 110 bearings can each be sized, shaped and configured to create a press fit between the pin 116 and the first 108 and second 110 bearings. The sizes of these components of the elbow prosthesis 100 can be small, and, for at least this reason, it can be difficult to assemble the bearing assembly 230 onto the ulnar component 104.

Described herein is an example of an assembly tool that can be used for assembling the bearing assembly 230 onto the ulnar component 104 of the elbow prosthesis 100 described above. Although the assembly tool is described for use in assembling components of an elbow prosthesis, the assembly tool described herein can similarly be used for other types of prostheses.

Figure 7:
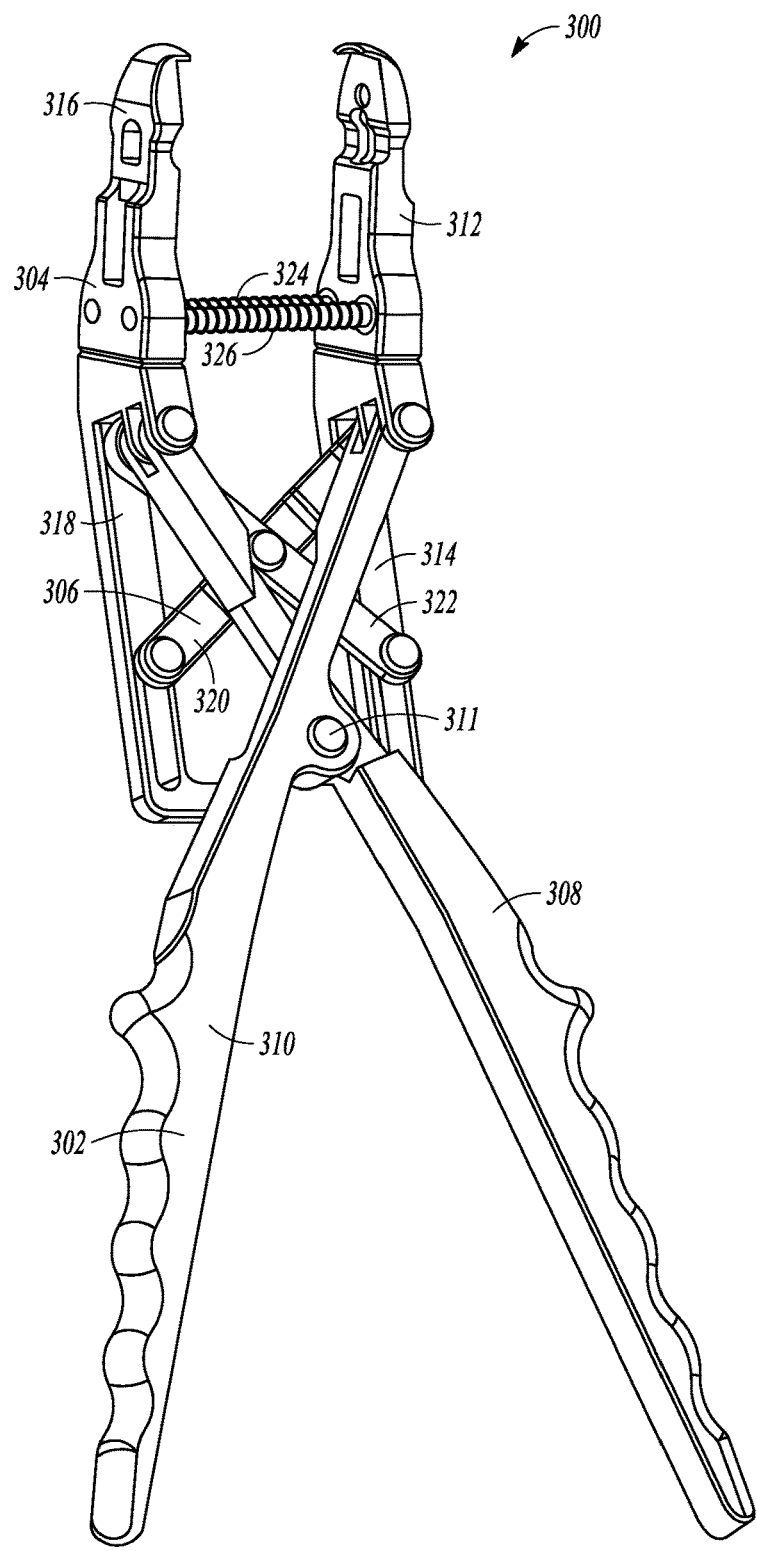
FIG. 7 is a front perspective view of an assembly tool in accordance with the present patent application.

FIG. 7 is a front perspective view of an assembly tool 300 which can include a handle assembly 302, a finger assembly 304, and a crossbar assembly 306. The handle assembly 302 can include a first handle 308 and a second handle 310. The first 308 and second 310 handles can be oriented in a scissor-like configuration and can be pivotally connected to each other by a pin 311. The finger assembly 304 can include a first finger 312 having a first finger extension 314 and a second finger 316 having a second finger extension 318. The crossbar assembly 306 can include a first crossbar 320 and a second crossbar 322. The crossbar assembly 306 can be attached to both the handle assembly 302 and the finger assembly 304, as described in further detail below.

Figure 8A:
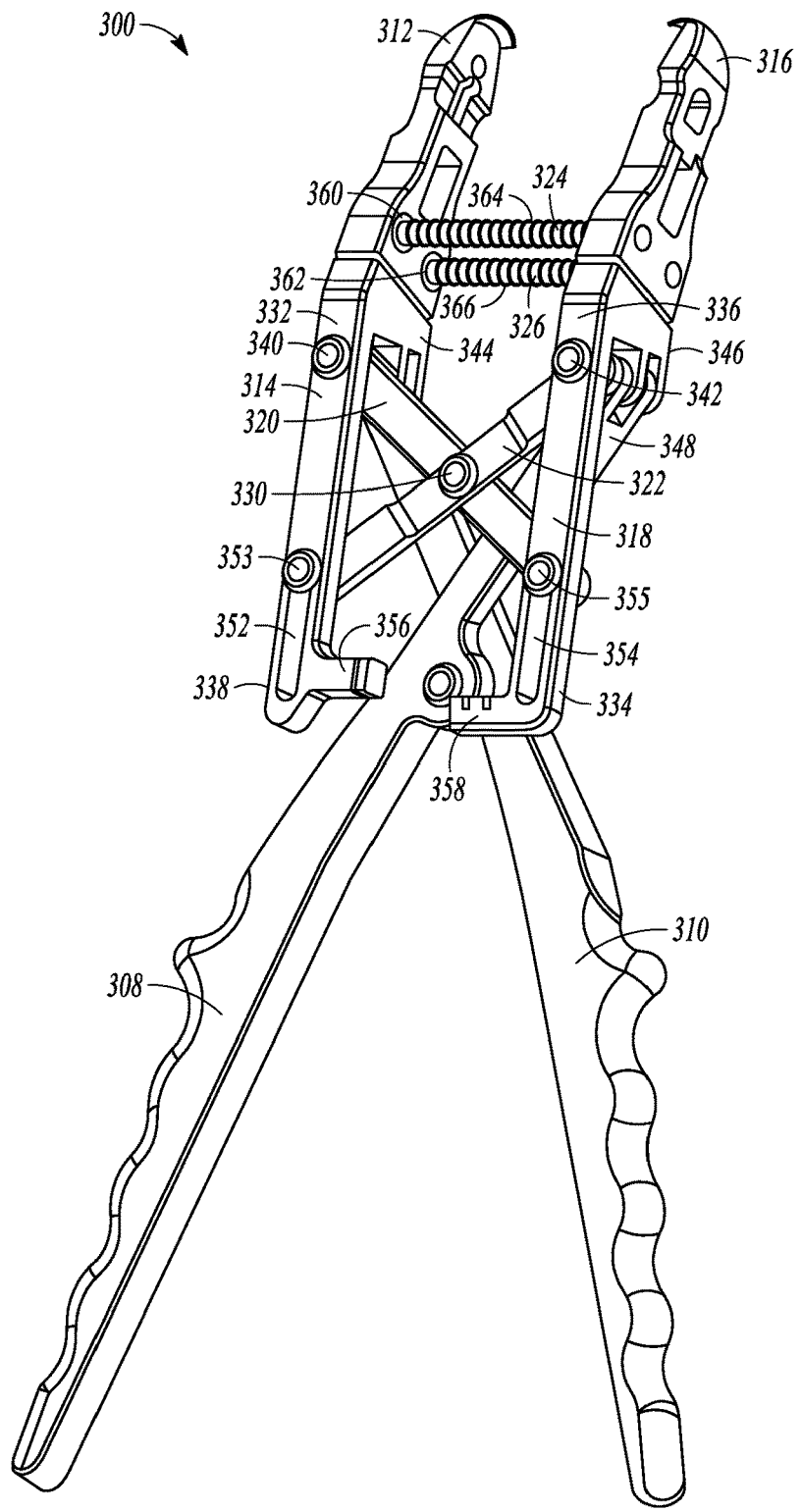
FIG. 8A is a rear perspective view of the assembly tool of FIG. 7 in a relaxed position.

The finger assembly 304 can be sized, shaped, and configured to engage components of the ulnar bearing assembly 230 shown in FIG. 6 above. As described in further detail below and shown in FIGS. 9A and 9B, the first 312 and/or second 316 fingers can include features configured to engage with features on the first 108 and second 110 bearings of the elbow prosthesis 100, which are part of the bearing assembly 230. The first 308 and second 310 handles can be sized, shaped, and configured to move the first 312 and second 316 fingers towards and away from each other. The finger assembly 304 can include at least one pin extending between the first 312 and second 316 fingers. As shown in FIGS. 7 and 8A, the finger assembly 304 can include a first guide pin 324 and a second guide pin 326.

The assembly tool 300 can be configured such that the first 312 and second 316 fingers, including the first 314 and second 318 finger extensions, remain substantially parallel to each other throughout movement of the first 312 and second 316 fingers by the first 308 and second 310 handles. The crossbar assembly 306 can be sized, shaped and configured to maintain the first 312 and second 316 fingers in a substantially parallel orientation relative to each other.

FIG. 8A is a rear perspective view of the assembly tool 300 further illustrating the crossbar assembly 306 and other features of the assembly tool 300. The first 320 and second 322 crossbars can be connected to each other by a pin 330, which can create a center pivot point. More specifically, the first 320 and second 322 crossbars can be connected to each other at a mid-point on each of the first 320 and second 322 crossbars. The first crossbar 320 can be connected to a top portion 332 of the first finger extension 314 and to a bottom portion 334 of the second finger extension 318. The second crossbar 322 can be connected to a top portion 336 of the second finger extension 318 and to a bottom portion 338 of the first finger extension 314. The first crossbar 320 can be connected to the second handle 310 and the second crossbar 322 can be connected to the first handle 308. More specifically, the first crossbar 320 can be connected to the second handle 310 via the same connection used to connect the first crossbar 320 to the first finger extension 314. This connection can include a pin 340 that extends through the first finger extension 314, the first crossbar 320 and the second handle 310. Similarly, the second crossbar 322 can be connected to the first handle 308 via the same connection used to connect the second crossbar 322 to the second finger extension 318, for example, using a pin 342 that extends through the second finger extension 318, the second crossbar 322 and the first handle 308.

As shown in FIG. 8A, in an example, the first 314 and second 318 finger extensions can each have a fork configuration 344 and 346, respectively, at the top portions 332 and 336 of the first 314 and second 318 finger extensions, respectively. Similarly, the handles 308 and 310 can each have a fork configuration—a fork configuration 348 on the first handle 308 is shown in FIG. 8A. The fork configurations on the finger extensions 314 and 318 and the fork configurations on the handles 308 and 310 can provide additional structural support and stability for connecting the finger extensions 314 and 318 to the crossbar assembly 306 and the handle assembly 302. In an example, one or both of the handles 308 and 310 and/or one or both of the first 314 and second 318 finger extensions can exclude the fork configurations included in the design shown in FIG. 8A.

The bottom portion 338 of the first finger extension 314 can include a slot 352 that a pin 353 can extend through to connect the second crossbar 322 to the first finger extension 314. Similarly, the bottom portion 334 of the second finger extension 318 can include a slot 354 that a pin 355 can extend through to connect the first crossbar 320 to the second finger extension 318. The slots 352 and 354 can facilitate vertical movement of the pins 353 and 355, respectively, in response to movement of the finger assembly 304 by the handle assembly 302, as described further below.

The first 314 and second 318 finger extensions can include a first gage portion 356 and a second gage portion 358, respectively, which can extend from the bottom portions 338 and 334 of the finger extensions 314 and 318, respectively. The gage portions 356 and 358 are discussed in further detail below in reference to FIGS. 8C and 8D.

The finger assembly 304 can include the first 324 and second 326 guide pins, which can each extend between the first 312 and second 316 fingers. Each of the guide pins 324 and 326 can be received in an aperture near a bottom portion of the corresponding first 312 and second 316 fingers. A first end of the first guide pin 324 can be received in and extend through a first aperture 360 in the first finger 312 and a first end of the second guide pin 326 can be received in and extend through a second aperture 362 in the first finger 312. A second end of the first guide pin 324 can be received in a first aperture in the second finger 316 and a second end of the second guide pin 326 can be received in a second aperture in the second finger 316.

Figure 8B:
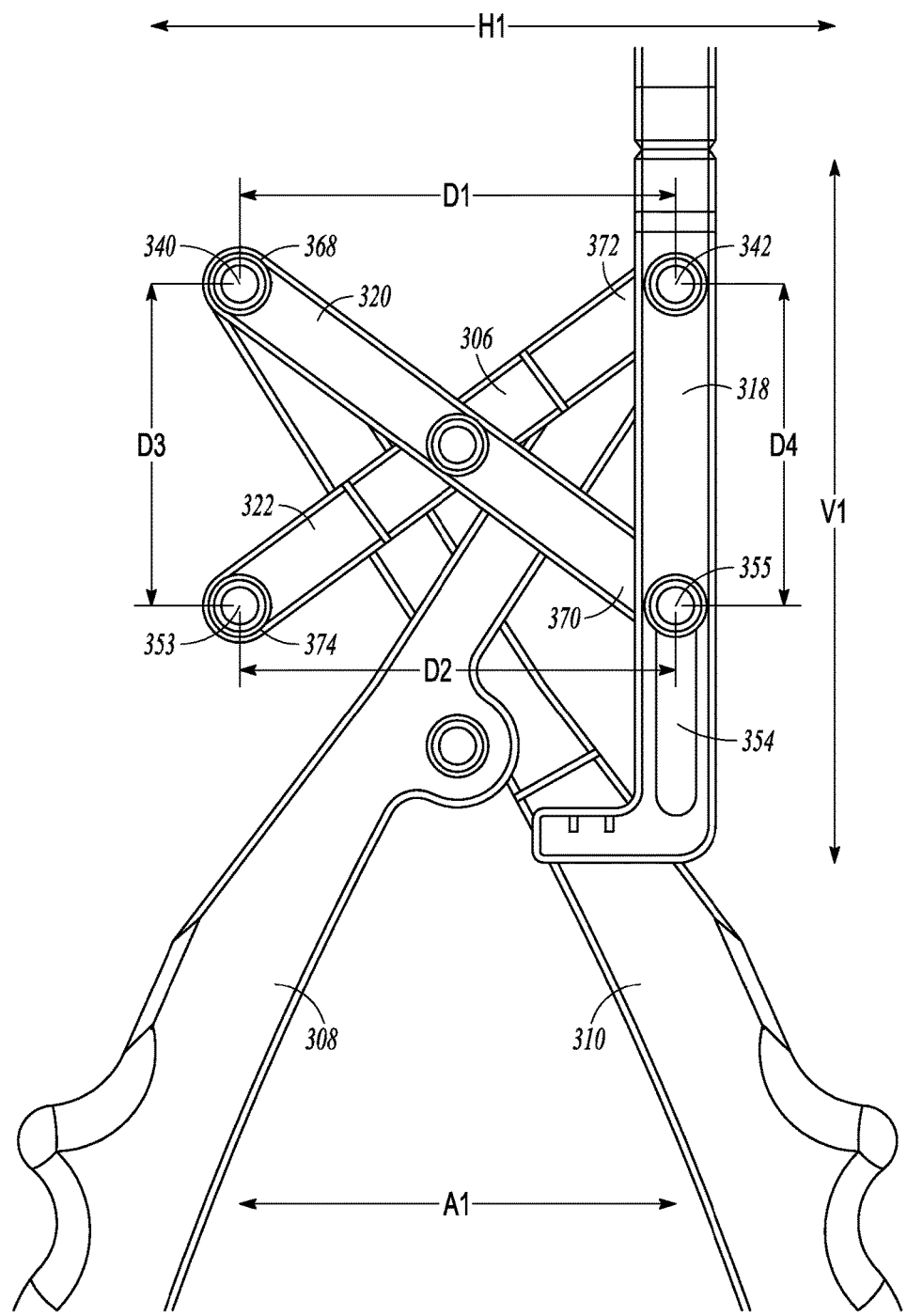
FIG. 8B is an enlarged view of a portion of the assembly tool of FIG. 8A.
Figure 8C:
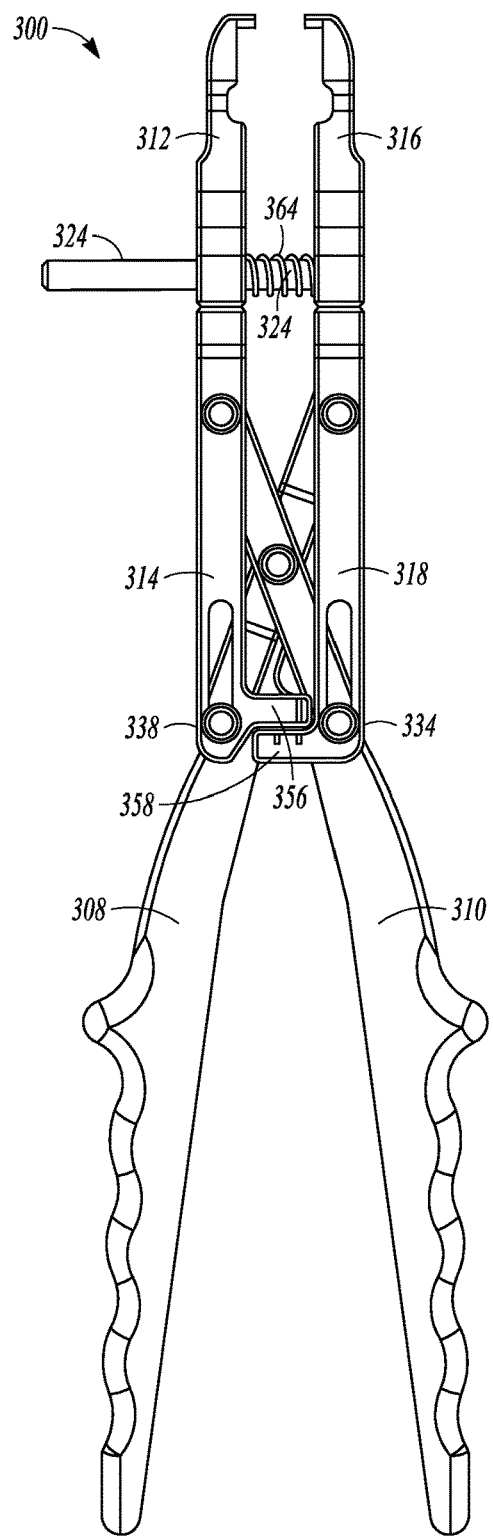
FIG. 8C is a perspective view of the assembly tool of FIG. 8A in a closed position.

In an example, the first 360 and second 362 apertures of the first finger 312 can extend through the first finger 312 such that the guide pins 324 and 326 can extend through an outside of the first finger 312 (as shown in FIG. 8C), and in contrast, the apertures in the second finger 316 do not extend through the second finger 316 such that the guide pins 324 and 326 cannot extend through to an outside of the second finger 316.

A first spring 364 can be wrapped around the first guide pin 324 and a second spring 366 can be wrapped around the second guide pin 326. When the first 312 and second 316 fingers are moved toward each other, by way of the handles 308 and 310, the springs 364 and 366 can compress. As the fingers 312 and 316 are brought closer together, a greater portion of the guide pins 324 and 326 can extend through the first 360 and second 362 apertures in the first finger 312 (see FIG. 8C). In another example, the apertures 360 and 362 of the first finger 312 do not extend through the first finger 312, and rather, the apertures in the second finger 316 can extend through the second finger 316 such that the guide pins 324 and 326 can extend through an outside of the second finger 316 as the fingers 312 and 316 are brought closer together. In yet another example, the apertures 360 and 362 in the first finger 312 can extend through the first finger 312 and the apertures in the second finger 316 can extend through the second finger 316 such that the guide pins 324 and 326 can extend through the outside of both the first 312 and second 316 fingers as the fingers 312 and 316 are brought closer together.

FIG. 8B shows a portion of the assembly tool 300 of FIG. 8A, which includes the first 308 and second 310 handles, the first 320 and second 322 crossbars, and the second finger extension 318, to aid in explaining how the crossbar assembly 306 can be configured to maintain the first 312 and second 316 fingers in a substantially parallel orientation to each other throughout movement of the first 312 and second 316 fingers by the handle assembly 302. The first crossbar 320 can include a top portion 368 and a bottom portion 370. The second crossbar 322 can include a top portion 372 and a bottom portion 374.

A user can grasp and squeeze the handles 308 and 310 in order to actuate or move the handles 308 and 310 towards each other, as shown in FIG. 8C. Thereafter, releasing or reducing the squeezing force on the handles 308 and 310 can move the handles 308 and 310 away from each other, eventually returning to a natural or relaxed position of FIG. 8B. A direction of movement of the handles 308 and 310 towards and away from each other is represented by arrow A1 in FIG. 8B. Movement of the handles 308 and 310 can result in movement of the first 320 and second 322 crossbars in both a vertical and horizontal direction, as further described below. A substantially vertical movement or direction can be represented by arrow V1 in FIG. 8B and a substantially horizontal movement or direction can be represented by arrow H1 in FIG. 8B.

As the handles 308 and 310 move towards each other, the top portions 368 and 372 of the first 320 and second 322 crossbars, respectively, can be configured to move towards each other. Similarly, as the handles 308 and 310 move away from each other and return to a relaxed position, the top portions 368 and 372 can be configured to move away from each other. When the top portions 368 and 372 move towards (or away) from each other, the bottom portions 370 and 374 of the first 320 and second 322 crossbars, respectively, also move towards (or away) from each other in a substantially equal amount. Throughout movement of the handles 308 and 310, a distance D1 between the top portions 368 and 372 can be substantially the same as a distance D2 between the bottom portions 370 and 374.

A distance between the top portion 368 of the first crossbar 320 and the bottom portion 374 portion of the second crossbar 322 can be defined as a distance D3. A distance between the top portion 372 of the second crossbar 322 and the bottom portion 370 of the first crossbar 320 can be defined as a distance D4. Similar to the distances D1 and D2 being substantially equal to each other, the distances D3 and D4 can be substantially equal to each other throughout movement of the handles 308 and 310.

As the handles 308 and 310 move towards each other, the distances D1 and D2 decrease. Reducing the distances D1 and D2 can result in increasing the distances D3 and D4. To accommodate an increase in the distances D3 and D4, the first 314 and second 318 finger extensions can include the slots 352 and 354, respectively, which can permit the bottom portions 370 and 374 of the first 320 and second 322 crossbars, respectively, to generally travel in a vertical direction (V1) in response to a decrease or increase in the distances D3 and D4.

Because each of the first 314 and second 318 finger extensions can be connected to the crossbar assembly 306, movement of the first 320 and second 322 crossbars can result in movement of the first 312 and second 316 fingers towards and away from each other. The use of the crossbars 320 and 322 and the slots 352 and 354 in the first 314 and second 318 finger extensions, respectively, can maintain the fingers 312 and 316 substantially parallel to each other throughout movement of the fingers 312 and 316.

Other crossbar designs in addition to, or as an alternative to, the crossbar assembly 306 described herein can be used as part of the assembly tool 300.

FIG. 8C shows the assembly tool 300 in a compressed or closed position in which the handles 308 and 310 can be squeezed as close together as the design permits, which results in the first 312 and second 316 fingers being generally as close together as they will go. As shown in FIG. 8C, when the fingers 312 and 316 are close together, a larger portion of the guide pins 324 and 326 can extend outside of the first finger 312 (only guide pin 324 is shown in FIG. 8C). The springs 364 and 366, which can be wrapped around the guide pins 324 and 326, respectively, can compress between the fingers 312 and 316.

Figure 8D:
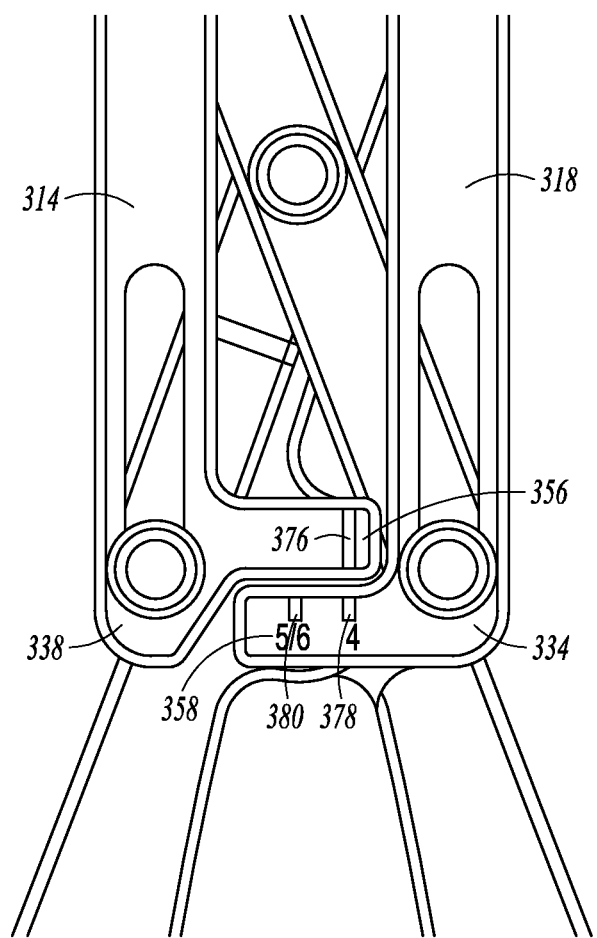
FIG. 8D is an enlarged view of a portion of the assembly tool of FIG. 8C.

The first finger extension 314 can include the first gage portion 356 that extends from the bottom portion 338 of the first finger extension 314. The second finger extension 318 can include the second gage portion 358 that extends from the bottom portion 334 of the second finger extension 318. The first 356 and second 358 gage portions can be used in combination to form a site gage for the user of the assembly tool 300. FIG. 8D is an enlarged view of a portion of the assembly tool 300 of FIG. 8C to better illustrate the site gage formed by the first 356 and second 358 gage portions. The site gage can be used, for example, if the assembly tool 300 is used to assemble a prosthesis or a component of the prosthesis that may already be implanted inside a patient's body. In an example, the ulnar component 104 (see FIG. 3) can already be installed or implanted into a patient's ulna (through the ulnar medullary canal) and then the assembly tool 300 can be used to assemble the bearing assembly 230 onto the implanted ulnar component 104. In that case, the user of the assembly tool 300 may not have visual access to the fingers 312 and 316 to know a position of the fingers 312 and 316 relative to each other, and whether the fingers 312 and 316 need to be brought closer together for assembly of the bearing assembly 230 onto the ulnar component 104.

The first gage portion 356 can include a reference marker 376 and the second gage portion 358 can include a first marker 378 and a second marker 380. As an example, the first marker 378 can be used to designate a Size 4 implant, and the second marker 380 can be used to designate a Size 5 or a Size 6 implant. When a user has squeezed the handles 308 and 310 such that the reference marker 376 on the first gage portion 356 is aligned with the first marker 378 on the second gage portion 358, the user can confirm that the first 312 and second 316 fingers are a sufficient distant apart for assembly of the bearing assembly 230 for a Size 4 implant. Similarly, for a Size 5 or Size 6 implant, because the implant is generally larger, the ulnar component 104 and the bearing assembly 230 are also generally larger, thus the user does not have to squeeze the fingers 312 and 316 as close together during assembly. When a user has squeezed the handles 308 and 310 such that the reference marker 376 is aligned with the second marker 380 on the second gage portion 358, the fingers 312 and 316 are sufficiently close together for assembly of the bearing assembly 230 for a Size 5 or Size 6 implant. Other types of size identifiers can be used on gage portions 356 and 358 in addition to or as an alternative to the Size 4, 5 and 6 identifiers shown in FIGS. 8C and 8D.

The markers 376, 378, and 380 can be etched onto the first 356 and second 358 gage portions, or the markers 376, 378, and 380 can be formed using any known method of creating a mark or notch. In an example, the second gage portion 358 can have more or less than the two markers 378 and 380 shown in FIGS. 8C and 8D. In an example, the reference marker 376 can be on the second gage portion 358 and the first 378 and second 380 markers can be on the first gage portion 356. Other designs in addition to, or as an alternative to, what is shown in FIGS. 8C and 8D can be used as a site gage for the assembly tool 300.

Figure 9A:
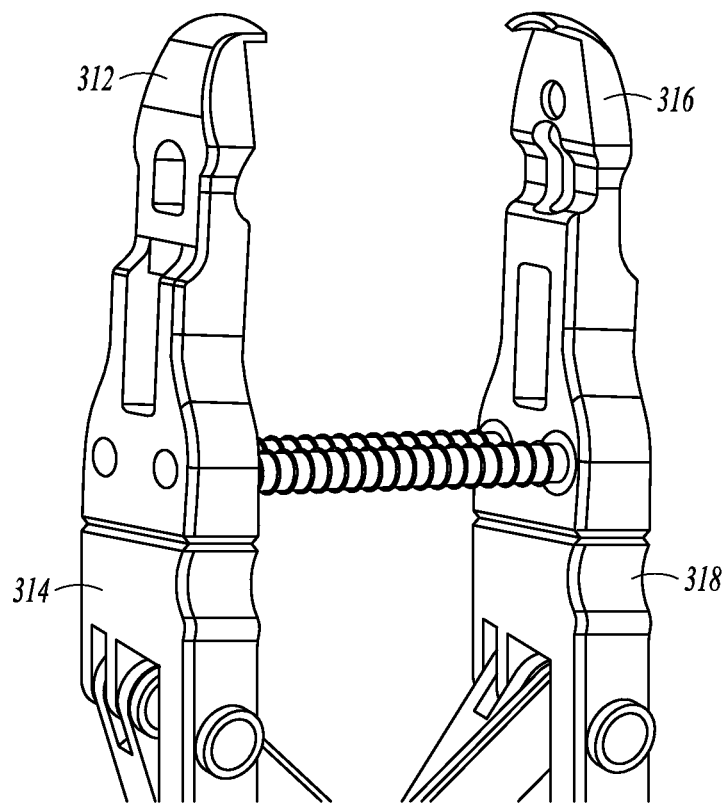
FIG. 9A is a perspective view of a portion of the assembly tool of FIG. 7.
Figure 9B:
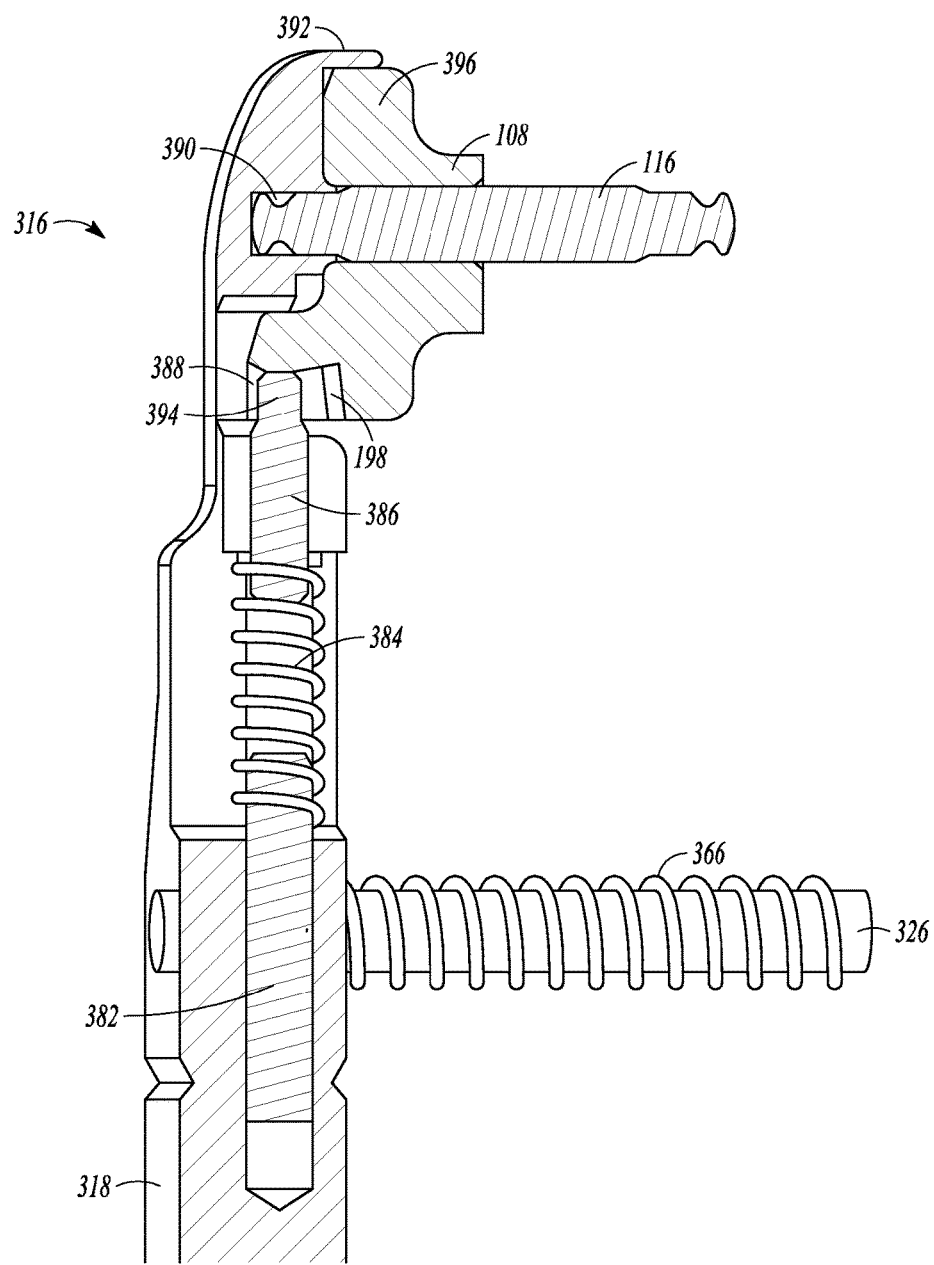
FIG. 9B is an enlarged view of a portion of the assembly tool of FIG. 9A.

FIG. 9A shows a portion of the assembly tool 300 to better illustrate the finger assembly 304, which can include the first 312 and second 316 fingers, and the first 314 and second 318 finger extensions. As further described below, the first 312 and second 316 fingers can be sized, shaped, and configured to engage various components of the elbow prosthesis 100 during assembly of at least some of the components of the prosthesis 100, such as, for example, the assembly of the bearing assembly 230 on the ulnar component 104. In an example, the first 312 and second 316 fingers can be sized, shaped, and configured to releasably engage the pin 116 (see FIG. 4) and the first 108 and second 110 ulnar bearings (see FIGS. 5A and 5B), all of the elbow prosthesis 100. FIG. 9B is a partial view of the finger assembly 304 shown in FIG. 9A and shows an inside view of the second finger 316, to better illustrate its features. In FIG. 9B, the second finger 316 is shown in engagement with the pin 116 and the first ulnar bearing 108.

In an example, the first 312 and second 316 fingers can be substantially the same; and the first 314 and second 318 finger extensions can be substantially the same. Although the second finger 316, and its corresponding features, is described in detail in reference to FIG. 9B, the first finger 312 can include substantially the same features.

The second finger 316 and the second finger extension 318 can be connected to each other using known connection means. In an example, the second finger 316 and the second finger extension 318 can be welded together. In another example, the second finger 316 and the second finger extension 318 can be integrally formed together. The second finger 316 can include a support pin 382, a spring 384, a finger pin 386, a recess 388, an axle pin aperture 390, and an overhang 392. The finger pin 386 can be movable in a vertical direction given its connection to the spring 384, which can be stabilized by the support pin 382. The recess 388 can be configured to releasably receive a feature on the ulnar bearing 108 and releasably secure the ulnar bearing 108 to the second finger 316. More specifically, in an example, the recess 388 can be configured to releasably receive the tab 198 on the ulnar bearing 108, as discussed further below. The axle pin aperture 390 can be configured to releasably receive the pin 116, also referred to as an axle pin, of the elbow prosthesis 100, as discussed further below.

A method of assembling the bearing assembly 230 on the ulnar component 104 is illustrated below in FIGS. 10-15. The engagement of the pin 116 and the first ulnar bearing 108 with the second finger 316 is included here to describe the various features of the second finger 316 that facilitate the releasable engagement of the pin 116 and the first ulnar bearing 108. FIG. 12 shows a step in the assembly method in which the pin 116 and the first ulnar bearing 108 can be releasably engaged with the second finger 316.

To releasably engage the first ulnar bearing 108 with the second finger 316, a user can place the first ulnar bearing 108 into the second finger 316 such that the tab 198 on the ulnar bearing 108 can be aligned with the recess 388. As such, a top portion 394 of the finger pin 386 can be received within the slot 199 on the first ulnar bearing 108, adjacent to the tab 198 (see FIGS. 5A and 5B). The user can push down on the first ulnar bearing 108 near a region 396 on the first ulnar bearing 108; as such, the slot 199 can push on the finger pin 386, which can be attached to the spring 384. As the first ulnar bearing 108 pushes on the finger 386, the spring 384 can compress. The first ulnar bearing 108 can fit under the overhang 392 of the second finger 316, which can help to temporarily or releasably secure the first ulnar bearing 108 in place. Once the first ulnar bearing 108 is in place with the region 396 in engagement with the overhang 392, the finger pin 386 maintains contact with the slot 199 on the first ulnar bearing 108. In an example, as shown in FIG. 9B, the first ulnar bearing 108 can have two points of contact with the second finger 316—a first point of contact can be between the finger pin 386 and the slot 199; a second point of contact can be between the overhang 392 and the region 396 of the first ulnar bearing 108.

The axle pin aperture 390 on the second finger 316 can be configured to temporarily receive or hold the pin 116. The pin 116 can be manually inserted into the axle pin aperture 390 by the user. The pin 116 can have a loose to moderate engagement with the aperture 390 such that the aperture 390 can temporarily hold the pin 116 in place; thus the second finger 316 can releasably engage the pin 116. In an example, the engagement of the pin 116 with the second finger 316 can be less constrained than the above described engagement (or securement) of the ulnar bearing 108 with the second finger 316.

Other designs can be used for the first 312 and second 316 fingers in addition to, or as an alternative to, the design described above in reference to FIGS. 9A and 9B. The first 312 and second 316 fingers can include additional or alternative features such that the fingers 312 and 316 can have releasable engagement with the ulnar bearing 108 and the pin 116.

The assembly tool 300 can be made of one or more materials suitable for use in surgical procedures for humans or animals. These materials can include, but are not limited to, stainless steel, titanium, cobalt, or one or more alloys thereof. In an example, some or all of the components of the assembly tool 300 can be made of stainless steel. In such a case, some of the components may be made of a first type of stainless steel and other components may be made of at least a second type of stainless steel. In an example, the type of material selected for a particular component can depend, in part, on whether that component articulates relative to another component.

FIGS. 10-15 illustrate a method 400 of using the assembly tool 300 to assemble multiple components onto an implant body. In an example, the components are the bearing assembly 230 and the implant body is the ulnar component 104, which are part of the elbow prosthesis 100 shown in the figures and described above. As shown in FIG. 6, the bearing assembly 230 can include the first ulnar bearing 108, the second ulnar bearing 110, and the pin 116.

Figure 10:
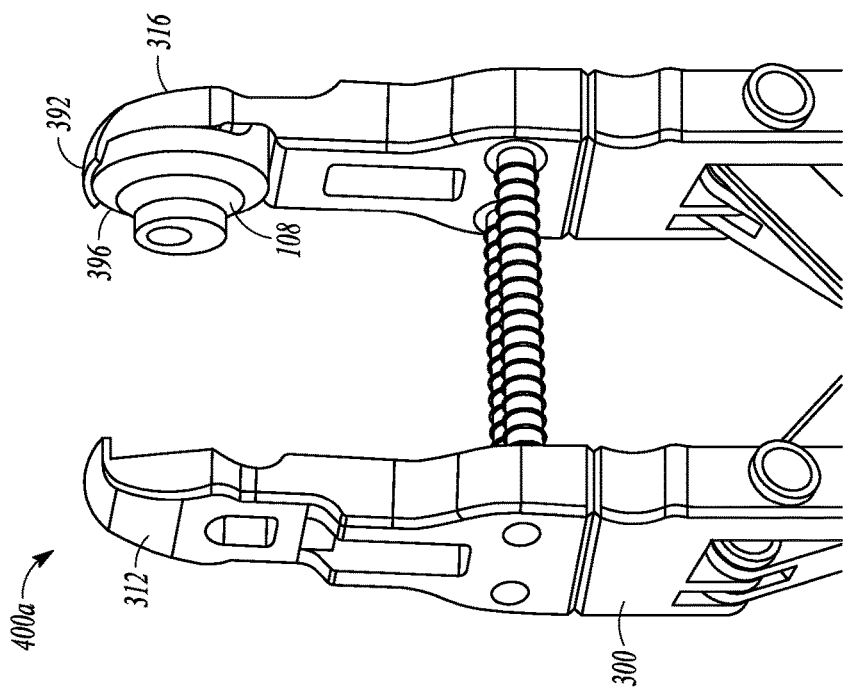

FIG. 10 illustrates a first step 400a in assembling the ulnar bearing assembly 230 onto the ulnar component 104, using the assembly tool 300 of FIGS. 7-9B and described above.

Specifically, the first step 400a can include releasably securing the first ulnar bearing 108 to the second finger 316 of the assembly tool 300. This step can be performed manually by the user. As described above in reference to FIG. 9B, the first ulnar bearing 108 can be placed on the second finger 316 such that the finger pin 386 can contact the first ulnar bearing 108 and thereby releasably secure the first ulnar bearing 108 to the second finger 316. The overhang 392 can also help to temporarily or releasably secure the first ulnar bearing 108.

Figure 11:
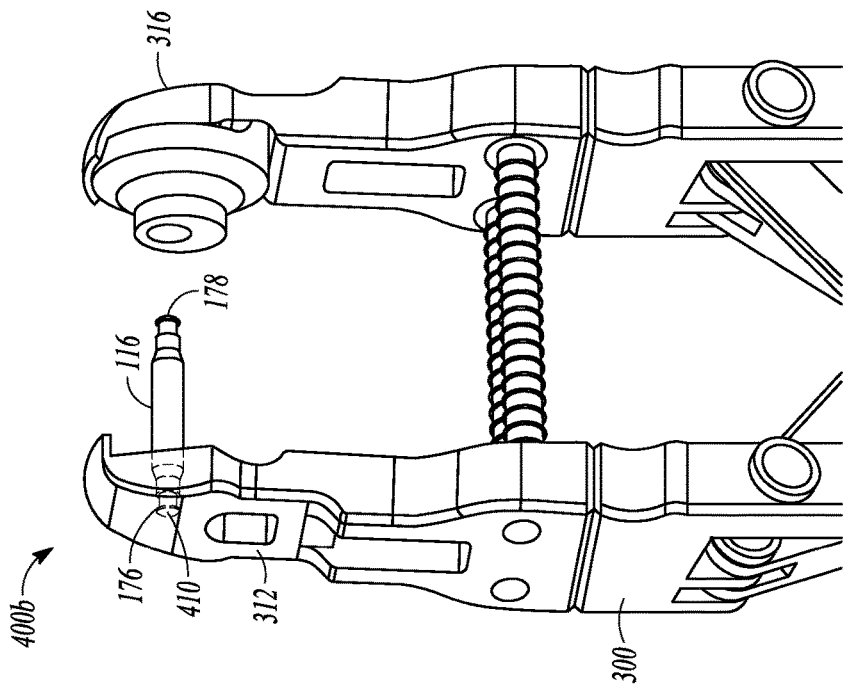
FIGS. 10-15 are perspective views of the assembly tool of FIG. 7 to illustrate steps in a method of using the assembly tool of FIG. 7 to assemble multiply components onto an implant body.
Figure 12:
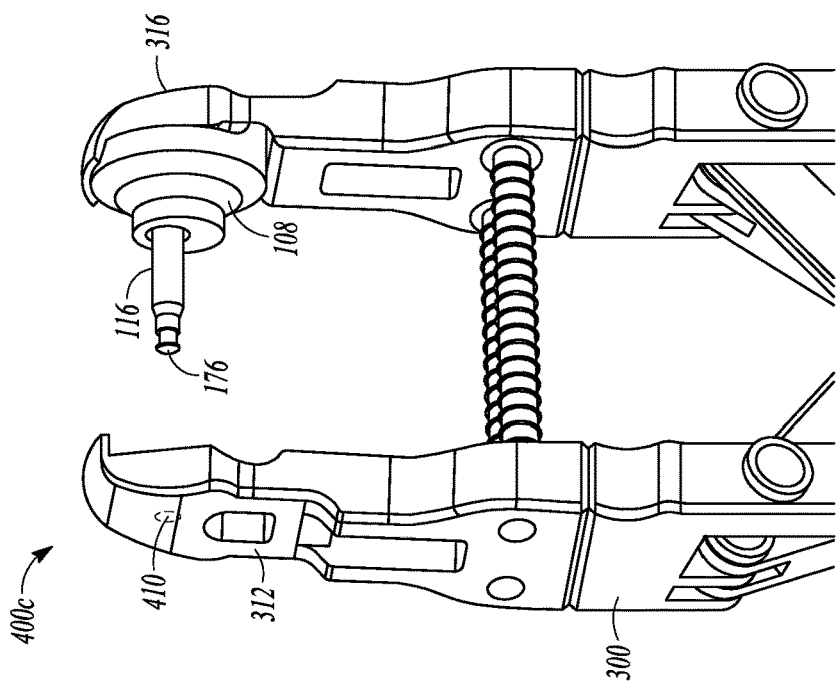

FIG. 11 illustrates a second step 400b in assembling the ulnar bearing assembly 230 on the ulnar component 104, and can include releasably engaging the pin 116 with the first finger 312. This step can also be performed manually by the user. The user can insert the first end portion 176 of the pin 116 into an axle pin aperture 410 in the first finger 312, which is similar to the axle pin aperture 390 of the second finger 316 described above in reference to FIG. 9B. Alternatively, the user can insert the second end portion 178 of the pin 116 into the axle pin aperture 410, particularly since the first 176 and second 178 end portions of the pin 116 can be substantially similar.

FIG. 12 illustrates a third step 400c in the assembly and can include moving or transferring the pin 116 from the first finger 312 to the second finger 316. The step 400c can be performed to allow for a next step in which the second ulnar bearing 110 can be releasably secured to the first finger 312, as described below in a fourth step 400d.

To move the pin 116 from the first finger 312 to the second finger 316, the user can squeeze the handles 308 and 310 together until the assembly 300 is generally in the closed position (see FIG. 8C), during which the second end portion 178 of the pin 116 (see FIG. 11) can engage with the first ulnar bearing 108 and the axle pin aperture 390 of the second finger 316 (see FIG. 9B). As described above in reference to FIGS. 5A and 5B, the pin 116 can have a press fit with the first 108 and second 110 ulnar bearings, and the shape of the bearings 108 and 110 and the pin 116 can facilitate such a press fit. Thus when the assembly 300 is in the closed position (see FIG. 8C), the pin 116 can be press fit to the first ulnar bearing 108 and releasably engaged with both the first 312 and second 316 fingers.

When the user starts to release the handles 308 and 310, the first end portion 176 of the pin 116 can release from the first finger 312 because an engagement of the first end portion 176 of the pin 116 in the aperture 410 of the first finger 312 can be weaker than the press fit securement of the second end portion 178 of the pin 116 to the first ulnar bearing 108.

Figure 13:
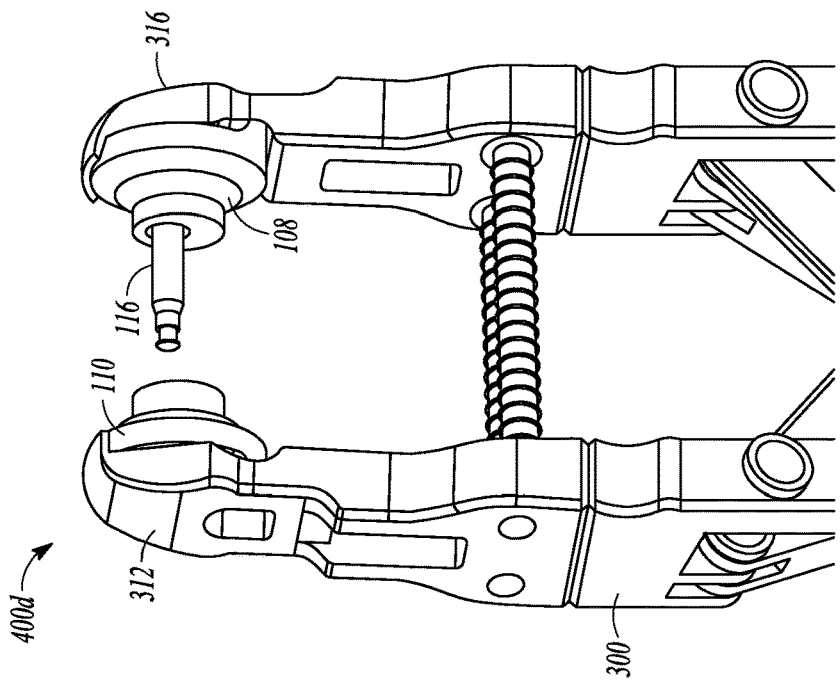

In the fourth step 400d of the method 400, shown in FIG. 13, the user can releasably secure the second ulnar bearing 110 to the first finger 312 as similarly described above for the first ulnar bearing 108 in reference to FIG. 10. At this point, all the components of the bearing assembly 230 (the first ulnar bearing 108, the second ulnar bearing 110, and the pin 116) can be releasably secured to or releasably engaged with the assembly tool 300.

Figure 14:
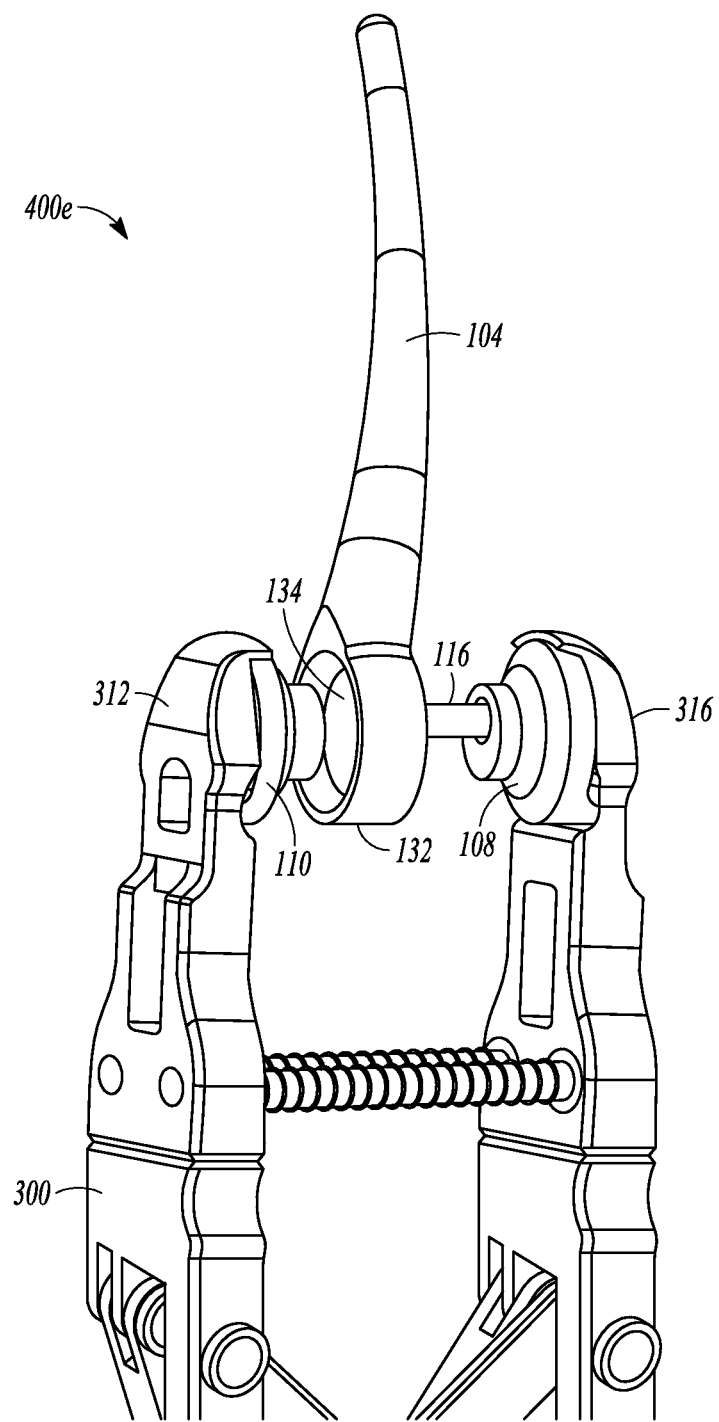

In a fifth step 400e, shown in FIG. 14, the assembly tool 300 and the components of the bearing assembly 230 can be placed near and around the ulnar component 104 in preparation for assembling the bearing assembly 230 onto the ulnar component 104. The steps 400a-400d can be performed independently of the patient and the ulnar component 104; thus the user of the assembly tool 300 can visually see the steps 400a-400d as they occur. In contrast, in the fifth step 400e, the assembly tool 300 and the components of the bearing assembly 230 can be positioned near the ulnar component 104.

In an example, the ulnar component 104 can already be implanted inside the patient's ulnar medually canal prior to assembling the bearing assembly 230 onto the ulnar component 104. In that case, the user can have a limited amount of space to work with and/or limited to no visual access to the area around the ulnar component 104 where the bearing assembly 230 is to be mounted to the ulnar component 104. Thus, the user can rely on the site gage (see FIGS. 8C-8D) described above, which can include the first 356 and second 358 gage portions. The fifth step 400e can include squeezing the handles 308 and 310 together until the assembly 300 is generally in a closed position or substantially closed position. The first 356 and second 358 gage portions can be used to determine when the closed position is achieved, which can depend on a size of the ulnar component 104 and relatedly, a size of the elbow prosthesis 100 overall.

When the fingers 312 and 316 are brought together in the fifth step 400e, the pin 116 can extend through the aperture 134 of the ulnar head 132 and the second ulnar bearing 110. The pin 116 can form a press fit with the second ulnar bearing 110. When the fingers 312 and 316 are brought together, the first bearing extension 208 of the first ulnar bearing 108 (see FIG. 5B) and a second bearing extension of the second ulnar bearing 110 can extend into the aperture 134 of the ulnar head 132. Once the fingers 312 and 316 are substantially closed, the end face 212 of the first ulnar bearing 108 (see FIG. 5B) can contact an end face on the second ulnar bearing 110.

Figure 15:
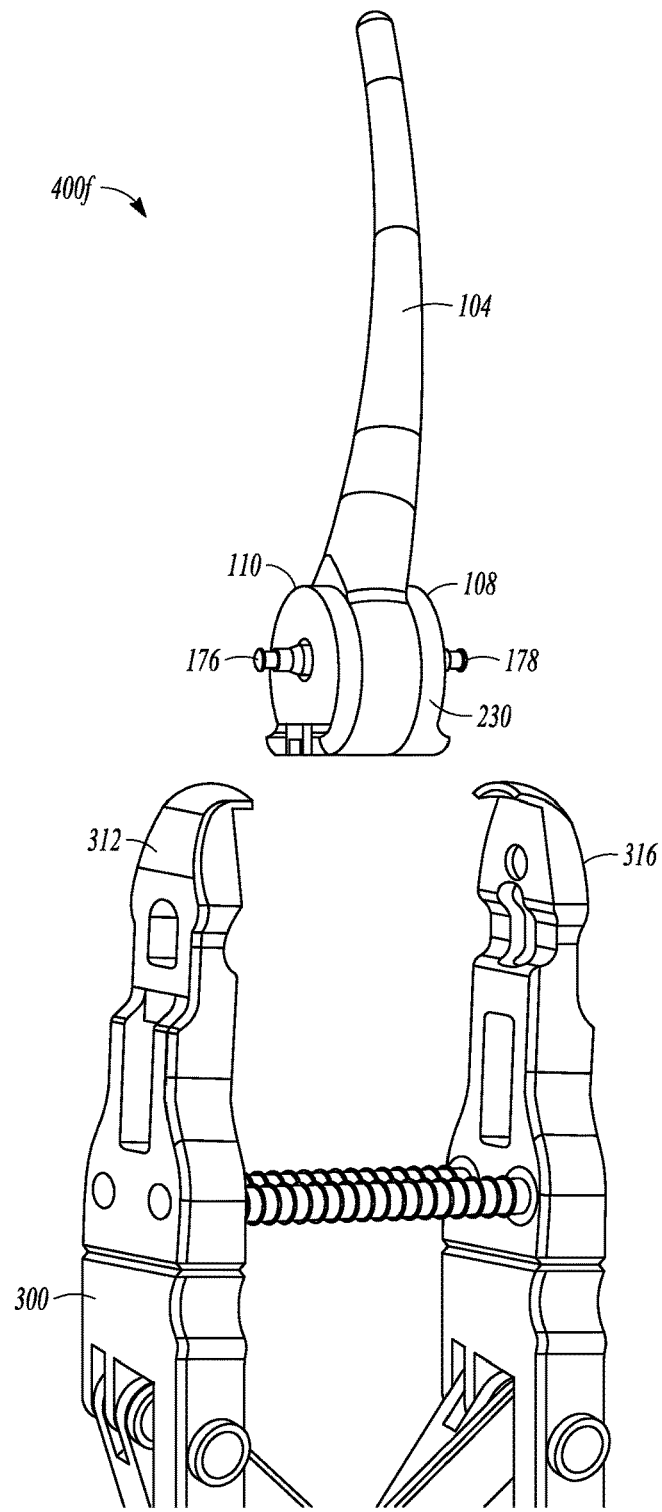

FIG. 15 illustrates a sixth step 400f of the method 400 in which the handles 308 and 310 can be released and the assembly 300 can be returned to a relaxed position. The fingers 312 and 316 can move away from each other, and as that happens, the first 176 and second 178 end portions of the pin 116 can be released from the first 312 and second 316 fingers. As similarly described above in reference to FIG. 12, the first 176 and second 178 end portions of the pin 116 can release from the first 312 and second 316 fingers because the press fit of the pin 116 with the first 108 and second 110 ulnar bearings can be stronger than engagement of the pin 116 with the apertures 410 and 390 of the first 312 and second 316 fingers, respectively.

FIG. 15 shows the bearing assembly 230 on the ulnar component 104. At this point the assembly tool 300 and the ulnar component 104 can be separated. The ulnar component 104 can be ready for connection to the humeral component 102 of the elbow prosthesis 100, as described above in reference to FIG. 6.

FIGS. 10-15 show an exemplary method of assembling the bearing assembly 230 on the ulnar component 104. The exact steps can vary from what is shown above—for example, the first ulnar bearing 108 can be releasably secured to the first finger 312 in a first step, instead of being releasably secured to the second finger 316, as shown in FIG. 10. The first 312 and second 316 fingers can be substantially the same, and the first 108 and second 110 ulnar bearings can be substantially the same, thus allowing for flexibility in an order of the steps above.

Modifications can be made to the assembly tool 300 such that the assembly tool 300 can be used with other types of prostheses. For example, the fingers 312 and 316 can be modified to engage with other components in addition to or as an alternative to the components of the bearing assembly 230 as shown in the figures and described above.

The assembly tool 300 can be provided in combination with a prosthesis such that, for example, a user can have easy access to the assembly tool 300 during an implantation procedure for the prosthesis. In an example, a system and/or a kit for repairing an elbow joint of a patient can include the elbow prosthesis 100 and the assembly tool 300. In an example, the kit can include a plurality of prostheses of varying sizes and/or a plurality of components of varying sizes. The kit can include instructions for use of the assembly tool 300. In an example, the elbow prosthesis 100 and the assembly tool 300 can be separately provided to the user, but used in combination during the implant procedure. The assembly tool 300 can be reusable in a subsequent implantation procedure after undergoing sterilization.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An assembly tool for assembling components of a multi-component implant, the assembly tool comprising:
    a finger assembly comprising:
    a first finger sized and shaped to releasably engage a first component of the implant, the first finger having a first feature configured to engage with a first portion of the first component and a second feature configured to engage with a second portion of the first component, wherein the first and second features are spaced apart from each other along a first longitudinal axis of the first finger and configured to independently engage with the first and second portions of the first component, and wherein a structure of each of the first and second features are different from each other such that each of the first and second features engage the first component in a different way relative to each other;
    a second finger sized and shaped to releasably engage a second component of the implant, the second finger having a third feature configured to engage with a first portion of the second component and a fourth feature configured to engage with a second portion of the second component, wherein the third and fourth features are spaced apart from each other along a second longitudinal axis of the second finger and configured to independently engage with the first and second portions of the second component, wherein a structure of each of the third and fourth features are different from each other such that each of the third and fourth features engage the second component in a different way relative to each other, and wherein the first and second longitudinal axes are oriented substantially parallel to each other;
    a handle assembly comprising a first handle pivotally connected to a second handle, the handle assembly configured to control movement of the first and second fingers when the first and second handles are actuated; and
    a crossbar assembly connected to the finger assembly and the handle assembly, the crossbar assembly configured to maintain the first and second fingers substantially parallel to each other during movement of the first and second fingers by actuation of the first and second handles,
    wherein each of the second and fourth features of the first and second fingers, respectively, is a pin configured for engagement with a recess in the first and second components, respectively, of the implant, and wherein the pin is connected to a spring such that the pin is movable in a direction corresponding to the longitudinal axis of the respective finger.

2. The assembly tool of claim 1, wherein the finger assembly comprises first and second finger extensions extending from the respective first and second fingers, and the crossbar assembly is attached to the first and second finger extensions.

3. The assembly tool of claim 2, wherein the crossbar assembly comprises:
    a first crossbar connected to a top portion of the first finger extension and a bottom portion of the second finger extension; and
    a second crossbar connected to a top portion of the second finger extension and a bottom portion of the first finger extension, wherein the first and second crossbars are connected to each other at a mid-point of each of the first and second crossbars.

4. The assembly tool of claim 3, wherein the first handle is connected to the top portion of the second finger extension and a top portion of the second crossbar, and the second handle is connected to the top portion of the first finger extension and a top portion of the first crossbar.

5. The assembly tool of claim 2, wherein the crossbar assembly has two points of connection to each of the first and second finger extensions and one point of connection to each of the first and second handles.

6. The assembly tool of claim 1 further comprising:
a pin extending between the first and second fingers; and
a spring wrapped around the pin, wherein the spring is compressible when the first and second fingers are moved closer to each other and the pin is configured to extend through an aperture in at least one of the first and second fingers when the first and second fingers are moved closer together.

7. The assembly tool of claim 1, wherein each of the first and third features of the first and second fingers, respectively, is an overhang that extends from a top of the respective finger in a direction generally perpendicular to the longitudinal axis of the respective finger.

8. The assembly tool of claim 1, wherein the aperture of the first finger is located on the first finger between the first and second features, and the aperture of the second finger is located on the second finger between the third and fourth features.

9. An assembly tool for assembling a multi-component implant, the assembly tool comprising:
a first finger including a first attachment feature configured to releasably secure a first component of the implant to the first finger;
a second finger including a second attachment feature configured to releasably secure a second component of the implant to the second finger, wherein each of the first and second attachment features includes a compressible component, and the first and second fingers are oriented substantially parallel to each other;
a handle assembly comprising a first handle pivotally connected to a second handle, the handle assembly configured to control movement of the first and second fingers when the first and second handles are actuated;
a first finger extension extending from the first finger and connected to the second handle;
a second finger extension extending from the second finger and connected to the first handle; and
a crossbar assembly comprising a first crossbar pivotally connected to a second crossbar, the crossbar assembly configured to maintain the first and second fingers substantially parallel to each other throughout movement of the first and second fingers by actuation of the first and second handles, wherein the compressible component of the first attachment feature includes a pin located inside the first finger and connected to a spring, and the compressible component of the second attachment feature includes a pin located inside the second finger and connected to a spring.

10. The assembly tool of claim 9, wherein the first crossbar is connected to a top portion of the first finger extension and a bottom portion of the second finger extension, the second crossbar is connected to a top portion of the second finger extension and a bottom portion of the first finger extension, and the first and second crossbars are connected to each other at a mid-point of each of the first and second crossbars.

11. The assembly tool of claim 10, wherein the first handle is connected to the top portion of the second finger extension and a top portion of the second crossbar, and the second handle is connected to the top portion of the first finger extension and a top portion of the first crossbar.

12. The assembly tool of claim 11, wherein a first pin extends through the first handle, the top portion of the second finger extension and the top portion of the second crossbar, and a second pin extends through the second handle, the top portion of the first finger extension and the top portion of the first crossbar.

13. The assembly tool of claim 10, wherein the first finger extension comprises:
a first slot in the bottom portion of the first finger extension; and
a first pin extending through the bottom portion of the second crossbar and the first slot in the first finger extension, such that the first pin is movable inside the slot when the first and second handles are actuated; and
the second finger extension comprises:
a second slot in the bottom portion of the second finger extension; and
a second pin extending through the bottom portion of the first crossbar and the second slot in the second finger extension, such that the second pin is movable inside the slot when the first and second handles are actuated.

14. The assembly tool of claim 9, wherein each of the first and second fingers includes an overhang that extends from a top of the respective finger in a direction generally perpendicular to a longitudinal axis of the respective finger, and an underside of the overhang of each of the first and second fingers is configured to releasably secure a top portion of the first and second components, respectively, of the implant.

15. The assembly tool of claim 14, wherein the first aperture is spaced between the overhang of the first finger and the first attachment feature, and the second aperture is spaced between the overhang of the second finger and the second attachment feature.

16. An assembly tool for assembling components of a multi-component implant, the assembly tool comprising:
a finger assembly comprising:
a first finger sized and shaped to releasably engage a first component of the implant, the first finger having a first feature configured to engage with a first portion of the first component and a second feature configured to engage with a second portion of the first component, wherein the first and second features are spaced apart from each other and configured to independently engage with the first and second portions of the first component; and
a second finger sized and shaped to releasably engage a second component of the implant, the second finger having a third feature configured to engage with a first portion of the second component and a fourth feature configured to engage with a second portion of the second component, wherein the third and fourth features are spaced apart from each other and configured to independently engage with the first and second portions of the second component, and wherein the first and second fingers are oriented substantially parallel to each other;
a handle assembly comprising a first handle pivotally connected to a second handle, the handle assembly configured to control movement of the first and second fingers when the first and second handles are actuated; and a crossbar assembly connected to the finger assembly and the handle assembly, the crossbar assembly configured to maintain the first and second fingers substantially parallel to each other during movement of the first and second fingers by actuation of the first and second handles, wherein each of the first and third features of the first and second fingers, respectively, is an overhang that extends from a top of the respective finger in a direction generally perpendicular to a longitudinal axis of the respective finger, and wherein each of the second and fourth features of the first and second fingers, respectively, is a pin centered around an axis parallel to the longitudinal axis of the respective finger and configured for engagement with a recess in the first and second components, respectively, of the implant.

17. The assembly tool of claim 16, wherein the pin is connected to a spring such that the pin is movable in a direction corresponding to the longitudinal axis of the respective finger.

* * * * *